US006949698B2

(12) United States Patent
Booth, Jr. et al.

(10) Patent No.: US 6,949,698 B2
(45) Date of Patent: Sep. 27, 2005

(54) GENE COMBINATIONS THAT ALTER THE QUALITY AND FUNCTIONALITY OF SOYBEAN OIL

(75) Inventors: John Russell Booth, Jr., Boothwyn, DE (US); Richard Martin Broglie, Landenberg, PA (US); William Dean Hitz, Landenberg, PA (US); Anthony John Kinney, Wilmington, DE (US); Susan Knowlton, Elkton, MD (US); Scott Anthony Sebastian, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 420 days.

(21) Appl. No.: 10/142,540

(22) Filed: May 10, 2002

(65) Prior Publication Data

US 2004/0049813 A1 Mar. 11, 2004

Related U.S. Application Data

(62) Division of application No. 09/303,592, filed on May 3, 1999, now Pat. No. 6,426,448.
(60) Provisional application No. 60/085,030, filed on May 11, 1998, and provisional application No. 60/085,423, filed on May 14, 1998.

(51) Int. Cl.[7] .................................................. A01H 5/00
(52) U.S. Cl. ........................ 800/312; 800/264; 800/281
(58) Field of Search ................................ 800/312, 264, 800/281

(56) References Cited

U.S. PATENT DOCUMENTS

| | | | | |
|---|---|---|---|---|
| 5,443,974 A | 8/1995 | Hitz et al. | ................ | 435/172.3 |
| 5,476,524 A | 12/1995 | Leon et al. | .................... | 47/58 |
| 5,516,980 A | 5/1996 | Fehr et al. | ................... | 800/200 |
| 5,530,183 A | 6/1996 | Fehr et al. | ................... | 800/200 |
| 5,530,186 A | 6/1996 | Hitz et al. | ................... | 800/205 |
| 5,534,425 A | 7/1996 | Fehr et al. | ................ | 435/172.1 |
| 5,557,037 A | 9/1996 | Fehr et al. | ................... | 800/200 |
| 5,585,535 A | 12/1996 | Fehr et al. | ................... | 800/200 |
| 5,602,311 A | 2/1997 | Fehr et al. | ................... | 800/200 |
| 5,602,317 A | 2/1997 | Luedtke, Jr. | ................ | 800/200 |
| 5,602,319 A | 2/1997 | Rhodes et al. | ............. | 800/200 |
| 5,638,637 A | 6/1997 | Wong et al. | .................... | 47/58 |
| 5,663,485 A | 9/1997 | Fehr et al. | ................... | 800/200 |
| 5,668,299 A | 9/1997 | Debonte et al. | ............ | 800/230 |
| 5,714,668 A * | 2/1998 | Fehr et al. | ................... | 800/312 |
| 5,714,669 A | 2/1998 | Fehr et al. | ................... | 800/200 |
| 5,972,412 A | 10/1999 | Sassen et al. | ................ | 426/603 |

FOREIGN PATENT DOCUMENTS

| | | | | |
|---|---|---|---|---|
| CA | 2180386 | 1/1998 | ............ | A01H/5/10 |
| WO | WO 92/11373 | 7/1992 | .......... | C12N/15/55 |
| WO | WO 92/20236 | 11/1992 | .......... | A23D/15/53 |
| WO | WO 93/11245 | 6/1993 | ........... | C12N/15/53 |
| WO | WO 94/11516 | 5/1994 | ........... | C12N/15/53 |
| WO | WO 94/18337 | 8/1994 | ........... | C12N/15/82 |
| WO | WO 95/07620 | 3/1995 | ............ | A23D/9/00 |
| WO | WO 96/06936 | 3/1996 | ........... | C12N/15/55 |
| WO | WO 97/40698 | 11/1997 | ............ | A23D/9/00 |
| WO | WO 98/04117 | 1/1998 | ............ | A01H/5/10 |

OTHER PUBLICATIONS

Schnebly, Steven R. et al., Inheritance of Reduced and Elevated Palmitate in Mutant Lines of Soybean, *Crop Science*, 34, 829–833, 1994.
Mattson, Fred H. et al., Comparison of effects of dietary saturated, monounsaturated, and polyunsaturated fatty acids on plasma lipids and lipoproteins in man, *Journal of Lipid Research*, 26, 194–202, 1985.
Knowles, P.F., Recent Advances in Oil Crops Breeding, *World Conference on Biotechnology for the Fats and Oil Industry Proceedings*, 35–38, 1980.
Allen, David, Fat modification as a tool for product development Part 1. Hydrogenation and fractionation, *Lipid Technology*, 10(2), 29–33, Mar. 1998.
Galliard, T., Degradation of Acyl Lipids: Hydrolytic and Oxidative Enzymes, *The Biochemisty of Plants*, 4, 85–116, 1980.
Erickson, E. A. et al., Inheritance of Altered Palmitic Acid Percentage in Two Soybean Mutants, *The Journal of Heredity*, 79, 465–468, 1988.
Mensink, Ronald P. et al., Effect of Dietary Trans Fatty Acids on High–Density and Low–Density Lipoprotein Cholesterol Levels in Healthy Subjects, *The New England Jouranl Of Medicine*, 323, No. 7, 439–445, Aug. 16, 1990.
Knutzon, Deborah S. et al., Modification of *Brassica* seed oil by antisense expression of a stearoyl–acyl carrier protein desaturase gene, *Pro. Natl. Acad. Sci. USA*, 89, 2624–2628, Apr. 1992.
Hammond, E.G. et al., Registration of A5 Germplasm Line of Soybean (Reg. No. GP44) and Registration of A6 Germplasm Line of Soybean (Reg. No. GP45), *Crop Science*, 23, 192–193, Feb. 1983.
Fehr, W.R. et al., Inheritance of Reduced Palmitic Acid Content in Seed Oil of Soybean, *Crop Science*, 31, 88–89, 1991.
Graef, G.L. et al., Fatty Acid Development in a Soybean Mutant with High Stearic Acid, *JAOCS*, 62, No. 4, 773–775, Apr. 1985.
Bafor, M. et al., Properties of the Glycerol Acylating Enzymes in Microsomal Preparations from the Developing Seed of Saflower (*Carthamus tinctorius*) and Turnip Rape (*Brassica campestris*) and their Ability to Assemble Coco-a–Butter Type Fats, *JAOCS*, 67 No. 4, No. 217–225, Apr. 1990.
Hardwood, John, Lipid Metabolism, *Critical Reviews in Plant Sciences*, 8, Issue 1, 1–43, 1989.

* cited by examiner

*Primary Examiner*—Elizabeth F. McElwain

(57) ABSTRACT

Novel gene combinations resulting in novel lipid profiles of soybean seeds and oil extracted from such seeds are disclosed. Methods for making such combinations are also described. In addition, the oils of this invention are disclosed to be useful in the manufacture of margarine and spread products.

3 Claims, 4 Drawing Sheets

GENE COMBINATIONS THAT ALTER THE QUALITY AND FUNCTIONALITY OF SOYBEAN OIL

FIELD OF THE INVENTION

This invention relates to novel gene combinations that result in novel lipid composition of soybean seeds and the oil extracted from such soybean seeds. These novel soybean gene combinations provide an alternative to the production of more expensive oils and to the chemical modification of oil to provide specific functional qualities and health attributes.

BACKGROUND OF THE INVENTION

Plant lipids have a variety of industrial and nutritional uses and are central to plant membrane function and climatic adaptation. These lipids represent a vast array of chemical structures, and these structures determine the physiological and industrial properties of the lipid. Many of these structures result either directly or indirectly from metabolic processes that alter the degree of unsaturation of the lipid. Different metabolic regimes in different plants produce these altered lipids, and either domestication of exotic plant species or modification of agronomically adapted species is usually required to economically produce large amounts of the desired lipid.

Plant lipids find their major use as edible oils in the form of triacylglycerols. The specific performance and health attributes of edible oils are determined largely by their fatty acid composition. Most vegetable oils derived from commercial plant varieties are composed primarily of palmitic (16:0), stearic (18:0), oleic (18:1), linoleic (18:2) and linolenic (18:3) acids. Palmitic and stearic acids are, respectively, 16- and 18-carbon-long, saturated fatty acids. Oleic, linoleic, and linolenic acids are 18-carbon-long, unsaturated fatty acids containing one, two, and three double bonds, respectively. Oleic acid is referred to as a mono-unsaturated fatty acid, while linoleic and linolenic acids are referred to as poly-unsaturated fatty acids. The relative amounts of saturated and unsaturated fatty acids in commonly used, edible vegetable oils are summarized below (Table 1).

TABLE 1

Percentages of Saturated and Unsaturated Fatty Acids in the Oils of Selected Oil Crops

|           | Saturated | Mono-unsaturated | Poly-unsaturated |
|-----------|-----------|------------------|------------------|
| Canola    | 6%        | 58%              | 36%              |
| Soybean   | 15%       | 24%              | 61%              |
| Corn      | 13%       | 25%              | 62%              |
| Peanut    | 18%       | 48%              | 34%              |
| Safflower | 9%        | 13%              | 78%              |
| Sunflower | 9%        | 41%              | 51%              |
| Cotton    | 30%       | 19%              | 51%              |

Many recent research efforts have examined the role that saturated and unsaturated fatty acids play in reducing the risk of coronary heart disease. In the past, it was believed that mono-unsaturates, in contrast to saturates and poly-unsaturates, had no effect on serum cholesterol and coronary heart disease risk. Several recent human clinical studies suggest that diets high in mono-unsaturated fat and low in saturated fat may reduce the "bad" (low-density lipoprotein) cholesterol while maintaining the "good" (high-density lipoprotein) cholesterol (Mattson et al. (1985) *Journal of Lipid Research* 26:194–202).

A vegetable oil low in total saturates and high in mono-unsaturates would provide significant health benefits to consumers as well as economic benefits to oil processors. As an example, canola oil is considered a very healthy oil. However, in use, the high level of poly-unsaturated fatty acids in canola oil renders the oil unstable, easily oxidized, and susceptible to development of disagreeable odors and flavors (Gailliard (1980) in *The Biochemistry of Plants* Vol. 4, pp. 85–116, Stumpf, P. K., ed., Academic Press, New York). The levels of poly-unsaturates may be reduced by hydrogenation, but the expense of this process and the concomitant production of nutritionally questionable trans isomers of the remaining unsaturated fatty acids reduces the overall desirability of the hydrogenated oil (Mensink et al. (1990) *New England J. Medicine* N323: 439–445). Similar problems exist with soybean oil and as noted in Table 1, commodity soybean oil typically contains over twice the saturated fat content of canola oil.

Mutation-breeding programs have met with some success in altering the levels of poly-unsaturated fatty acid levels found in the edible oils of agronomic species. Examples of commercially grown varieties are high (85%) oleic sunflower and low (2%) linolenic flax (Knowles (1980) in *World Conference on Biotechnology for the Fats and Oils Industry Proceedings,* Applewhite, T. H., ed., American Oil Chemists' Society, pp. 35–38). Similar commercial progress with the other plants shown in Table 1 has been elusive, largely due to the difficult nature of the procedure and the pleiotropic effects of the mutational regime on plant hardiness, yield potential and the environmental instability of the low poly-unsaturate trait. Above all, the inability to consistently produce an oil of defined composition from season to season and in differing locations has made the commercial production of low poly-unsaturate soybean oil infeasible.

The discovery of a method for altering the expression of the enzymes responsible for introduction of the second (international patent publication WO 94/11516) and third (international patent publication WO 93/11245) double bonds into soybean seed storage lipid in a directed manner has allowed the production of soybeans with a high mono-unsaturated, very low polyunsaturated fatty acid content and especially a very low linolenic acid content. The genetic combination of these two transgene profiles described in the instant invention leads to a soybean line with minimal poly-unsaturates and high mono-unsaturates and extreme environmental stability of the seed fatty acid profile.

Soybeans with decreased levels of saturated fatty acids have been described resulting from mutation breeding (Erickson, E. A. et al., (1994) *J. Hered.* 79:465–468; Schnebly, S. R. et al. (1994) *Crop Sci.* 34:829–833; and Fehr, W. R. et al. (1991) *Crop Sci.* 31:88–89) and transgenic modification (U.S. Pat. No. 5,530,186). The demonstration of the combination of these two traits in a single soybean line in this invention brings the health benefits of a high mono-unsaturate, low saturate oil to soybean production.

While oils with low levels of saturated fatty acids are desirable from the standpoint of providing a healthy diet, fats that are solid at room temperature are required for their functional properties in some foods. Such applications include the production of non-dairy margarines and spreads, and various applications in confections and in baking. Many animal and dairy fats provide the necessary physical properties, but they also contain both cholesterol and the cholesterogenic medium chain fatty acids. An ideal triglyceride for solid fat applications should contain a predominance of the very high melting, long chain fatty acid stearic acid and a balance of mono-unsaturated fatty acid with very little polyunsaturated fat. Natural plant solid fat fractions typically have a triacylglyceride structure with saturated fatty acids occupying the sn-1 and sn-3 positions of the triglycerides and an unsaturated fatty acid at the sn-2 position. This overall fatty acid composition and triglyceride structure confers an optimal solid fat crystal structure and a maximum melting point with minimal saturated fatty acid content.

The natural fat prototype for this high melting temperature vegetable fat is cocoa butter. The fatty acid composition of cocoa butter is 26% palmitic (16:0), 34% stearic (18:0), 35% oleic (18:1), and 3% linoleic(18:2) acids. This fatty acid profile gives cocoa butter a melting point range of from 25° to 36° C. depending upon its precise crystal structure. The high price and fluctuating supply of cocoa butter has led to several processes for the production of cocoa butter substitutes and margarine stocks by fractionating other oils with relatively high 18:0 content or catalytic hydrogenation of high polyunsaturated oils followed by fractionation of the product.

Oilseeds capable of producing directly high stearate, low polyunsaturate oils would be advantageous in that both the cost of hydrogenation and the undesirable side products of hydrogenation, trans monounsaturated fatty acids, could be avoided. In addition, the fractionation process could be made more cost effective or possibly eliminated if the melting temperature range of the vegetable fat produced were high enough.

Oil biosynthesis in plants has been fairly well-studied [see Harwood (1989) in *Critical Reviews in Plant Sciences*, Vol. 8 (1):1–43]. The biosyntheses of palmitic, stearic and oleic acids occur in the plastids by the interplay of three key enzymes of the "ACP track": palmitoyl-ACP elongase, stearoyl-ACP desaturase and the acyl-ACP thioesterases.

Of these three enzyme types, the acyl-ACP thioesterases function to remove the acyl chain from the carrier protein (ACP) and thus away from the metabolic pathway. Oleoyl-ACP thioesterase catalyzes the hydrolysis of oleoyl-ACP thioesters at relatively high rates, although it also catalyzes the hydrolysis of palmitoyl-ACP and stearoyl-ACP at much lower rates. This multiple activity leads to substrate competition between enzymes, and it is the competitions of acyl-ACP thioesterase and palmitoyl-ACP elongase for the same substrate and of acyl-ACP thioesterase and stearoyl-ACP desaturase for the same substrate that contributes to the production of the palmitic and stearic acids found in the triacylglycerides of vegetable oils.

Once removed from the ACP track, fatty acids are exported to the cytoplasm and there they are used to synthesize acyl-coenzyme A. These acyl-CoAs are the acyl donors for at least three different glycerol acylating enzymes (glycerol-3-P acyltransferase, 1-acyl-glycerol-3-P acyltransferase and diacylglycerol acyltransferase) which incorporate the acyl moieties into triacylglycerides during oil biosynthesis.

These acyltransferases show a strong, but not absolute, preference for incorporating saturated fatty acids at sn-1 and sn-3 positions and monounsaturated fatty acids at the sn-2 position of the triglyceride. Thus, altering the fatty acid composition of the acyl pool will drive a corresponding change in the fatty acid composition of the oil. Furthermore, there is experimental evidence that because of this specificity, plants can produce cocoa butter substitutes or other specialty fats if there is the correct composition of fatty acids available in the substrate pool for the acyltransferases [Bafor et al., (1990) *JAOCS* 67:217–225].

Based on the above discussion, one approach to changing the levels of palmitic, stearic and oleic acids in vegetable oils is to alter their levels in the cytoplasmic acyl-CoA pool used for oil biosynthesis.

Manipulation of stearate levels has been described (Knutzon, D. S. et al., (1992) *Proc. Natl Acad. Sci. USA* 89(7): 2624–2628). Seeds from both *B. campestris* and *B. napus* plants were produced by antisense expression of a cDNA encoding the *B. campestris* stearoyl-ACP desaturase, the enzyme responsible for introducing the first double bond into 18 carbon fatty acids in plants, using a seed specific promoter region. These seeds produced oils high in stearic acid, that also contained elevated levels of linolenic acid (18:3), when compared to seeds from unmodified plants from the same species. Elevated levels of stearic acid have been obtained in soybean by a similar underexpression of stearoyl-ACP desaturase (U.S. Pat. No. 5,443,974) and in canola by over expression of an acyl-ACP thioesterase (U.S. Pat. No. 5,530,186). Mutation breeding has also produced soybean lines with elevated levels of stearic acid in their seed oils (Graef, G. L. et al., (1985) *JAOCS* 62:773–775; Hammond, E. G. and W. R. Fehr, (1983) *Crop Sci.* 23:192–193).

Poly-unsaturated fatty acids contribute to the low melting point of liquid vegetable oils. In high saturate oils their presence is a detriment in that they decrease the melting point, and therefore even higher levels of undesirable saturated fatty acid are required to achieve a plastic fat at room temperature. Additionally, when used in baking and confectionery applications high levels of poly-unsaturates leads to oxidative instability as described above for liquid oils. Thus for maximum utility a high saturate fat produced in soybean should contain saturated fatty acids, mono-unsaturated fatty acid and as little poly-unsaturated fatty acid as possible. Gene combinations discovered in this invention provide novel fatty acid profiles in soybean which meet these criteria.

SUMMARY OF THE INVENTION

The present invention concerns a soybean plant that produces mature seeds in which the total seed fatty acid profile comprises a combined C16:0 and C18:0 content of greater than 21%, a C18:1 content of greater than 60% and a combined C18:2 and C18:3 content of less than 7%.

In a second embodiment, this invention concerns a soybean plant that produces mature seeds in which the total seed fatty acid profile comprises a C16:0 content of greater than 10%, a combined C16:0 and C18:0 content of greater than 30%, a C18:1 content of greater than 55% and a combined C18:2 and C18:3 content of less than 7%.

In a third embodiment, this invention concerns a soybean plant that produces mature seeds in which the total seed fatty acid profile comprises a combined C16:0 and C18:0 content of greater than 42% wherein said plant is produced by the following steps which comprise:
  (a) crossing a first parent soybean plant wherein the C18:0 content comprises at least 10% of the total seed fatty acid and the first parent further comprises at least one transgene copy of a nucleic acid fragment encoding an oleoyl-ACP thioesterase enzyme with a second parent comprising a fasa allele for elevated seed stearic acid content;

(b) obtaining hybrid seeds from the cross of step (a), germinating said seeds, growing and producing a segregating population of soybean plants through one or more cycles of self-pollination; and (c) selecting the plants from the segregating population of step (b) which produce seeds having said fatty acid profile.

In a fourth embodiment, this invention concerns a soybean plant that produces mature seeds in which the total seed fatty acid profile comprises a combined C16:0 and C18:0 content of less than 7%, a C18:1 content of greater than 87% and a combined C18:2 and C18:3 content of less than 6%.

In a fifth embodiment, this invention concerns a soybean plant that produces mature seeds in which the total seed fatty acid profile comprises a combined C16:0 and C18:0 content of less than 12%, a C18:1 content of greater than 84% and a combined C18:2 and C18:3 content of less than 5%.

In a sixth embodiment, this invention concerns the use of high stearic, or high stearic and high oleic, oils produced from the soybean plants described herein to produce margarine and/or spread products. Also, products made from hydrogenation, fractionation, interesterification, or hydrolysis of such oils can be used to produce margarines and/or spread products whether in a blended or unblended form.

In a seventh embodiment, this invention concerns the use of the high stearic acid, or stearic and high oleic, oils produced from the soybean plants described herein to produce margarine and/or spread products from blends with other oils. Also, products made from hydrogenation, fractionation, interesterification, or hydrolysis of such oils can be used to produce margarines and/or spread products whether in a blended or unblended form.

BIOLOGICAL DEPOSIT

The following soybean seed has been deposited with the American Type Culture Collection (ATCC), 10801 University Boulevard, Manassas, Va. 20110-2209, and bears the following designation, accession number and date of deposit.

| Soybean | Accession Number | Date of Deposit |
| --- | --- | --- |
| Soybean T1S | ATCC 203033 | May 14, 1998 |
| Soybean L9216116-109 | ATCC 203946 | Apr. 20, 1999 |

BRIEF DESCRIPTION OF THE FIGURES AND SEQUENCE DESCRIPTIONS

The invention can be more fully understood from the following detailed description, a description of the four figures, and the Sequence Descriptions which form a part of this application.

FIG. 1 depicts the Solid Fat Content (SFC) profiles of a high stearic, and four different high stearic and high oleic acid soybean oils compared to a soft tub vegetable oil spread. Only the 22% high stearic and high oleic (HS/HO A) performs as a spread product. The SFC profiles of the remaining oils indicated that these oils would not perform as a spread product.

FIG. 2 depicts the relative oxidative stabilities (OSI) of several unblended and blended oils. A high oleic acid content coupled with a low polyunsaturate content is necessary to achieve high oxidative stability. Blended oils such as soybean oil (SO) mixed with palm oil (PO), or high stearic (HS) oil mixed with palm oil or fully hydrogenated oil may perform well as margarine or spread products based upon SFC profile.

Figure 1:
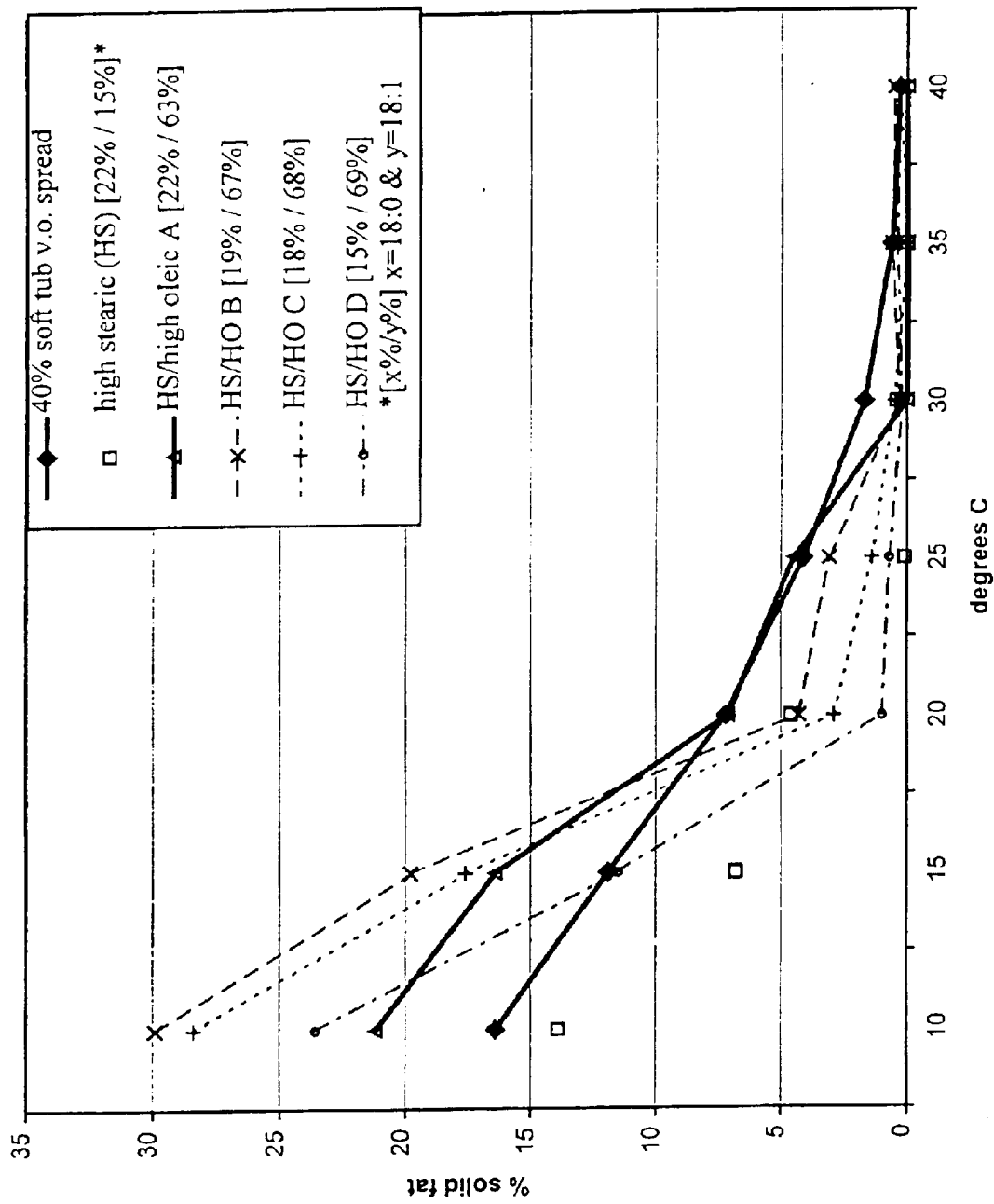

The sequence descriptions summarize the Sequences Listing attached hereto. The Sequence Listing contains one letter codes for nucleotide sequence characters and the three letter codes for amino acids as defined in the IUPAC-IUB standards described in *Nucleic Acids Research* 13:3021–3030 (1985) and in the *Biochemical Journal* 219 (No. 2):345–373 (1984), and the symbols and format used for all nucleotide and amino acid sequence data further comply with the rules governing nucleotide and/or amino acid sequence disclosures in patent applications as set forth in 37 C.F.R. §1.821–1.825 and WIPO Standard St.25. The nucleotide sequences read from 5' to 3'.

SEQ ID NO: 1 shows a 1412 base pair cDNA of an acyl-ACP thioesterase from *Brassica napus*.

SEQ ID NO:2 shows the amino acid sequence of the precursor protein of a *B. napus* seed acyl-ACP thioesterase (the coding sequence of SEQ ID NO: 1).

SEQ ID NO:3 shows the nucleotide sequence of a second acyl-ACP thioesterase cDNA from *Brassica napus*, corresponding to GenBank accession U17098.

SEQ ID NO:4 shows the amino acid sequence of the precursor protein of the second *B. napus* seed acyl-ACP thioesterase (the coding sequence of SEQ ID NO:3).

DETAILED DESCRIPTION OF THE INVENTION

A wide variety of novel soybean genes that alter oil quality have been discovered through selection for natural variation, mutation breeding, and genetic engineering. Certain soybean lines or combinations containing those novel genes are used in this disclosure and are referred to by the "Gene Combinations or Line Name" designations described in Table 2.

TABLE 2

Typical Fatty Acid Profiles of Soybeans
With Different Fatty Acid Modification Genes

| Gene Combination or Line Name[1] | Individual Fatty Acid Content (% of total seed fatty acid) | | | | | Reference |
| --- | --- | --- | --- | --- | --- | --- |
| | 16:0 | 18:0 | 18:1 | 18:2 | 18:3 | |
| wild type | 12 | 4 | 25 | 51 | 7 | — |
| T1S | 16 | 10 | 19 | 47 | 7 | Example 11, this application |
| D2T | 7 | 3 | 85 | 1 | 3 | WO 94/11516 |

TABLE 2-continued

Typical Fatty Acid Profiles of Soybeans
With Different Fatty Acid Modification Genes

| Gene Combination or Line Name[1] | Individual Fatty Acid Content (% of total seed fatty acid) | | | | | Reference |
|---|---|---|---|---|---|---|
| | 16:0 | 18:0 | 18:1 | 18:2 | 18:3 | |
| D3A | 10 | 5 | 32 | 49 | 3 | WO 93/11245 |
| fan | 11 | 3 | 45 | 36 | 4 | U.S. Pat. No. 5,534,425 |
| fap1 | 8 | 4 | 28 | 52 | 8 | U.S. Pat. No. 5,585,535 |
| fap2 | 16 | 4 | 19 | 53 | 8 | U.S. Pat. No. 5,850,029 |
| fap3 | 7 | 3 | 26 | 53 | 11 | U.S. Pat. No. 5,585,535 |
| fap1 × fap3 | 4 | 3 | 22 | 63 | 8 | U.S. Pat. No. 5,585,535 |
| fasa | 8 | 23 | 26 | 35 | 7 | U.S. Pat. No. 5,557,037 |
| L9216116-109 | 9 | 22 | 15 | 48 | 5 | Example 3, this application |
| N85-2176 | 11 | 3 | 42 | 40 | 4 | Kuhr et al., March 26, 1987, USDA Agric. Res. Services |
| HST1 | 9 | 28 | 15 | 43 | 5 | Example 3, this application |
| HO2 | 11 | 3 | 45 | 37 | 4 | Example 3, this application |
| HO4 | 11 | 3 | 45 | 37 | 4 | Example 3, this application |
| T2T | 3 | 2 | 17 | 65 | 12 | WO 9606936, Example 13, this application |

[1]The Gene Codes used in this Table refer to the following:
T1S refers to a oleoyl-ACP thioesterase expression construct which is in the sense orientation and expresses a functional enzyme.
D2T refers to a delta-12 desaturase construct which is in a sense orientation, the integration of which results in a reduction of activity.
D3A refers to a delta-15 desaturase construct which is in the antisense orientation, the integration of which results in a reduction of activity.
fan refers to a gene for decreased seed linolenic acid content.
fap1 refers to a gene for decreased seed palmitic acid content.
fap2 refers to a gene for elevated seed palmitic acid content.
fap3 refers to a gene for decreased seed palmitic acid content.
fasa refers to a gene for elevated seed stearic acid content.
L9216116-109 refers to a line with high stearic acid content derived from pedigree (HST1*(HO2*HO4))*wild-type.
HST1 refers to a high stearic acid mutant line derived from N85-2176.
HO2 refers to a high oleic acid mutant line derived from N85-2176.
HO4 refers to a high oleic acid mutant line derived from A5.
T2T refers to a palmitoyl-ACP thioesterase construct that is in the sense orientation, the integration of which results in a reduction of activity.

In the context of this disclosure, a number of terms shall be utilized. "Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "transgene" is a gene that has been introduced into the genome by a transformation procedure.

The expression "genetic locus", as used herein, means the position of a gene on a chromosome or set of chromosomes. The term "allele", as used herein, refers to any of the alternative forms of a genetic locus. The term "expression", as used herein, is intended to mean the production of a functional end-product. Expression or overexpression of a gene involves transcription of the gene and translation of the mRNA into precursor or mature protein. "Antisense inhibition" refers to the production of antisense RNA transcripts capable of preventing the expression of the target protein. "Overexpression" refers to the production of a gene product in transgenic organisms that exceeds levels of production in normal or non-transformed organisms. "Cosuppression" refers to the expression of a transgene which has substantial homology to an endogenous gene resulting in the suppression of expression of both the ectopic and the endogenous gene.

"Altered expression" refers to the production of gene product(s) in transgenic organisms in amounts or proportions that differ significantly from that activity in comparable tissue (organ and of developmental type) from wild-type organisms.

The terms "environmentally stable" or "environmental stability" as used herein are used to describe a phenotype that is relatively constant, regardless of the environmental conditions in which a plant is grown.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 153:277) and particle-accelerated or "gene gun" transformation technology (Klein et al. (1987) *Nature* (London) 327:70–73; U.S. Pat. No. 4,945,050).

As used herein, "soybean" refers to the species *Glycine max, Glycine soja,* or any species that is sexually cross compatible with *Glycine max*. A "line" is a group of plants of similar parentage that display little or no genetic variation between individuals for a least one trait. Such lines may be created by one or more generations of self-pollination and selection, or vegetative propagation from a single parent including by tissue or cell culture techniques. An "agronomically elite line" or "elite line" refers to a line with desirable agronomic performance that may or may not be used commercially. A "variety", "cultivar", "elite variety", or "elite cultivar" refers to an agronomically superior elite line that has been extensively tested and is or was being used for commercial soybean production. "Mutation" refers to a detectable and heritable genetic change (either spontaneous or induced) not caused by segregation or genetic recombination. "Mutant" refers to an individual, or lineage of individuals, possessing a mutation. As used herein, an "F1 population" is the progeny resulting from cross-pollinating one line with another line. The format used herein to depict such a cross-pollination is "female parent*male parent". An "F2 population" is the progeny of the self-pollinated F1 plants. An "F2-derived line" or "F2 line" is a line resulting from the self-pollination of an individual F2 plant. An F2-derived line can be propagated through subsequent generations (F3, F4, F5 etc.) by repeated self-pollination and bulking of seed from plants of said F2-derived line. A "segregating population" is a population of plants resulting from a cross that is at a stage of inbreeding of F2 or later.

The term "mature seed(s)" as used herein refers to a soybean that is no longer green that has, or did have, a moisture content less than 20%, and preferably less than 12%.

The term "fat product" as used herein refers to vegetable oils either in a natural (non-hydrogenated and non-chemically modified) form, or in a hydrogenated and/or chemically modified form, or fractions derived therefrom, either in a natural (non-hydrogenated and non-chemically modified) form, or in a hydrogenated and/or chemically modified form.

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989 (hereinafter "Maniatis").

The present invention concerns soybean lines with novel fatty acid compositions.

In one embodiment, this invention concerns a soybean plant that produces mature seeds in which the total seed fatty acid profile comprises a combined C16:0 and C18:0 content of greater than 21%, a C18:1 content of greater than 60% and a combined C18:2 and C18:3 content of less than 7%.

A soybean plant having such a fatty acid profile is produced by the following steps which comprise:

(a) crossing a first parent soybean plant wherein the C18:1 content comprises at least 80% of the total seed fatty acid and the first parent further comprises at least one transgene copy of a soybean nucleic acid fragment encoding a delta-12 desaturase enzyme with a second parent comprising either an appropriate transgene, or a mutation such as the fasa allele, that confers an elevated seed stearic acid content;

(b) obtaining hybrid seeds from the cross of step (a), germinating said seeds, growing and producing a segregating population of soybean plants through one or more cycles of self-pollination; and (c) selecting the plants from the segregating population of step (b) which produce seeds having said fatty acid profile.

Also of interest are seeds obtained from such a plant, oil obtained from these seeds, products made from the hydrogenation, fractionation, interesterification or hydrolysis of such oil and by-products made during the production of this oil. In addition, this invention also concerns the use of such oils, and the use of products made from the hydrogenation, fractionation, interesterification, or hydrolysis of such oils, to make a margarine or spread product whether in a blended or unblended form.

In a second embodiment, this invention concerns a soybean plant that produces mature seeds in which the total seed fatty acid profile comprises a C16:0 content of greater than 10%, a combined C16:0 and C18:0 content of greater than 30%, a C18:1 content of greater than 55% and a combined C18:2 and C18:3 content of less than 7%.

A soybean plant having such a fatty acid profile is produced by the following steps which comprise:

(a) crossing a first parent soybean plant wherein the C18:1 content comprises at least 80% of the total seed fatty acid and the first parent further comprises at least one transgene copy of a soybean nucleic acid fragment encoding a delta-12 desaturase enzyme with a second parent comprising chimeric transgenes that increase the content of both palmitic and stearic acid in the seeds, or an alternative wherein the second parent comprises mutations such as fasa for elevated seed stearic acid content and fap2 for elevated seed palmitic acid;

(b) obtaining hybrid seeds from the cross of step (a), germinating said seeds, growing and producing a segregating population of soybean plants through one or more cycles of self-pollination; and (c) selecting the plants from the segregating population of step (b) which produce seeds having said fatty acid profile.

Also of interest are seeds obtained from such a plant, oil obtained from these seeds, products made from the hydrogenation, fractionation, interesterification or hydrolysis of such oil and by-products made during the production of this oil. In addition, this invention also concerns the use of such oils and the use of products made from the hydrogenation, fractionation, interesterification or hydrolysis of such oils to make a margarine or spread product whether in a blended or unblended form.

In a third embodiment, this invention concerns a soybean plant that produces mature seeds in which the total seed fatty acid profile comprises a combined C16:0 and C18:0 content of greater than 42% wherein said plant is produced by the following steps which comprise:

(a) crossing a first parent soybean plant wherein the C18:0 content comprises at least 10% of the total seed fatty acid and the first parent further comprises at least one transgene copy of a nucleic acid fragment encoding an oleoyl-ACP thioesterase enzyme with a second parent comprising either an appropriate transgene, or a mutation such as the fasa allele, that confers an elevated seed stearic acid content;

(b) obtaining hybrid seeds from the cross of step (a), germinating said seeds, growing and producing a segregating population of soybean plants through one or more cycles of self-pollination; and (c) selecting the plants from the segregating population of step (b) which produce seeds having said fatty acid profile.

Also of interest are seeds obtained from such a plant, oil obtained from these seeds, products made from the hydrogenation, fractionation, interesterification or hydrolysis of such oil and by-products made during the production of this oil. In addition, this invention also concerns the use of such oils, products made from such oils, and blended products made from such oils that can be used to make a margarine or spread product.

In a fourth embodiment, this invention concerns a soybean plant that produces mature seeds in which the total seed fatty acid profile comprises a combined C16:0 and C18:0 content of less than 7%, a C18:1 content of greater than 87% and a combined C18:2 and C18:3 content of less than 6%.

A soybean plant having this fatty acid profile is produced by the following steps which comprise:

(a) crossing a first parent soybean plant wherein the C18:1 content comprises at least 80% of the total seed fatty acid and the first parent further comprises at least one transgene copy of a soybean nucleic acid fragment encoding a delta-12 desaturase enzyme with (i) a second parent comprising both a fap1 allele for decreased seed palmitic acid content and a fap3 allele for decreased seed pahnitic acid content, or (ii) the second parent comprises at least one transgene copy of a soybean nucleic acid fragment encoding a plant acyl-ACP thioesterase for decreased seed pahnitic acid content wherein said thioesterase has a preference of at least two-fold for palmitoyl-ACP over either stearoyl-ACP or oleoyl-ACP;

(b) obtaining hybrid seeds from the cross of step (a), germinating said seeds, growing and producing a segregating population of soybean plants through one or more cycles of self-pollination; and (c) selecting the plants from the segregating population of step (b) which produce seeds having said fatty acid profile.

Also of interest are seeds obtained from such a plant, oil obtained from these seeds, products made from the hydrogenation, fractionation, interesterification or hydrolysis of such oil and by-products made during the production of this oil.

In a fifth embodiment, this invention concerns a soybean plant that produces mature seeds in which the total seed fatty acid profile comprises a combined C16:0 and C18:0 content of less than 12%, a C18:1 content of greater than 84% and a combined C18:2 and C18:3 content of less than 5%.

A soybean plant having this fatty acid profile is produced by the following steps which comprise:

(a) crossing a first parent soybean plant wherein the C18:1 content comprises at least 80% of the total seed fatty acid and the first parent further comprises at least one transgene copy of a soybean nucleic acid fragment encoding a delta-12 desaturase enzyme with a second parent comprising either a mutation such as the fan allele for decreased seed linolenic acid content, or at least one transgene copy of a soybean nucleic acid fragment encoding a delta-15 desaturase enzyme and further wherein the C18:3 content comprises less than 4% of the total seed fatty acid;

(b) obtaining hybrid seeds from the cross of step (a), germinating said seeds, growing and producing a segregating population of soybean plants through one or more cycles of self-pollination; and (c) selecting the plants from the segregating population of step (b) which produce seeds having said fatty acid profile.

Also of interest are seeds obtained from such a plant, oil obtained from these seeds, products made from the hydrogenation, fractionation, interesterification or hydrolysis of such oil and by-products made during the production of this oil.

The general method used to assemble the specific genotypes responsible for the novel seed fatty acid profiles described herein is as follows:

1) Parental lines chosen for their seed fatty acid profile were cross-pollinated by manual transfer of pollen from the flowers of one parent plant to the emasculated flowers of the second parent plant.

2) Mature seeds from the cross pollinated flowers were planted to produce F1 plants which were allowed to self pollinate to produce an F2 population of seeds carrying varying doses of genes involved in producing the seed fatty acid phenotype of the two parents.

3) A small chip of the mature seed was removed from a portion of the cotyledon which is not in direct contact with the embryonic axis. The relative content of the five main fatty acids comprising the seed lipids was determined by gas liquid chromatography as described in WO 93/11245, and the remaining portions of seeds chosen on the basis of the fatty acid profile of the analyzed chip were planted. The chosen F2 plants were allowed to self pollinate and produce F3 seeds. The above analytical procedure was repeated on single seeds from this generation and on the bulk seed lot from this generation.

As an alternative, the F2 seed population can be grown and self pollinated without prior selection and bulk seed from individual plants in the resulting F2 plants analyzed to select F2:3 families on the basis of single plant bulk seed fatty acid analysis.

Once identified lines with desired fatty acid profiles can be advanced as self pollinated populations to maintain and test the seed fatty acid profile.

To produce lines with concomitantly high levels of oleic acid and low levels of poly-unsaturated fatty acids, a delta-12 desaturase down-regulated transgenic line described in WO 97/40698 was chosen as one parent. To produce soybean lines low in poly-unsaturates but high in saturated fatty acids a soybean line that contained a mutation resulting in high levels of stearic acid was chosen as the second parent. An example of such a line can be found in U.S. Pat. No. 5,557,037, the disclosure of which is hereby incorporated by reference. That patent discloses the soybean line A6 which carries a mutation at a locus designated as the fasa locus.

To produce lines with concomitantly high levels of oleic acid and very low levels of saturated fatty acids, the delta-12 desaturase down-regulated line was chosen as one parent, and a line with very low levels of palmitic acid was chosen as the second parent. One approach was to use a second parent containing a combination of genes, such a line can be found in U.S. Pat. No. 5,585,535, the disclosure of which is hereby incorporated by reference. Another approach is to use the line disclosed in WO 96/06936 as the second parent wherein a palmitoyl-ACP thioesterase construct is disclosed that is in the sense orientation, the integration of which results in a reduction of activity.

To further decrease the level of the poly-unsaturated fatty acid linolenic acid and to enhance the environmental stability of the low poly-unsaturated fatty acid phenotype the delta-12 desaturase down regulated transgenic line was chosen as one parent and either a transgenic line with down regulated expression of the delta-15 desaturase or a mutant line with a similar linolenic acid phenotype was chosen as the second parent. An example of a mutant line with a linolenic acid phenotype similar to that produced by down regulation of the delta-15 desaturase may be found in U.S. Pat. No. 5,534,425, the disclosure of which is hereby incorporated by reference.

Very high levels of saturated fatty acids in soybean seeds were produced by the combination of a mutant line producing seeds with high levels of stearic acid with a transgenic line carrying a chimeric gene for seed specific over-expression of a plant acyl-ACP thioesterase.

Methods for the extraction and processing of soybean seeds to produce soybean oil and meal are well known throughout the soybean processing industry. hi general, soybean oil is produced using a series of steps which accomplish the extraction and purification of an edible oil product from the oil bearing seed. Soybean oils and soybean byproducts are produced using the generalized steps shown in the diagram below.

| Process | Impurities Removed/ Byproducts Obtained |
|---|---|
| Soybean Seed ↓ | |
| Oil Extraction ↓ | → Meal |
| Degumming ↓ | → Lecithin |
| Alkali or Physical Refining ↓ | → Gums, Free Fatty Acids Pigments |
| Water Washing ↓ | → Soap |
| Bleaching ↓ | → Color, Soap, Metal |
| (Hydrogenation) ↓ | |
| (Winterization) ↓ | → Stearine |
| Deodorization ↓ | → FFA, Tocopherols, Sterols, Volatiles |
| Oil Products | |

Soybean seeds are cleaned, tempered, dehulled, and flaked which increases the efficiency of oil extraction. Oil extraction is usually accomplished by solvent (hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (antisticking) agents. Degummed oil may be further refined for the removal of impurities; primarily free fatty acids, pigments, and residual gums. Refining is accomplished by the addition of caustic which reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth which removes most of the chlorophyll and carotenoid compounds. The refined oil can be hydrogenated resulting in fats with various melting properties and textures. Winterization (fractionation) may be used to remove stearine from the hydrogenated oil through crystallization under carefully controlled cooling conditions. Deodorization which is principally steam distillation under vacuum, is the last step and is designed to remove compounds which impart odor or flavor to the oil. Other valuable by products such as tocopherols and sterols may be removed during the deodorization process. Deodorized distillate containing these byproducts may be sold for production of natural vitamin E and other high value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, 1995, Practical Handbook of Soybean Processing and Utilization, The American Oil Chemists' Society and United Soybean Board.

Hydrogenation is a chemical reaction in which hydrogen is added to the unsaturated fatty acid double bonds with the aid of a catalyst such as nickel. High oleic soybean oil contains unsaturated oleic, linoleic, and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables that affect the hydrogenation reaction which in turn alter the composition of the final product. Operating conditions including pressure, temperature, catalyst type and concentration, agitation and reactor design are among the more important parameters which can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings, used in the manufacture of baking products, solid fats and shortenings used for commercial frying and roasting operations, and base stocks for margarine manufacture are among the myriad of possible oil and fat products achieved through hydrogenation. A more detailed description of hydrogenation and hydrogenated products can be found in Patterson, H. B. W., 1994, Hydrogenation of Fats and Oils: Theory and Practice. The American Oil Chemists' Society.

Hydrogenated oils have also become controversial due to the presence of trans fatty acid isomers that result from the hydrogenation process. Ingestion of large amounts of trans isomers has been linked with detrimental health effects including increased ratios of low density to high density lipoproteins in the blood plasma and increased risk of coronary heart disease. It would be advantageous to produce foods that currently use hydrogenated oils in a form that would be free of trans fatty acids. The term "substantially free of trans fatty acids" as used herein means a non-health threatening level of trans fatty acids. For example, such a level can range from 0.1% (i.e., an amount which cannot be reliably detected by current methods for assessing trans fatty acid levels) to an upper limit which does not pose a health risk. In the near future, the Federal government is expected to place an upper limit on the levels of trans fatty acid isomers that can be present in foods and have the designation "trans fatty acid free". It is believed that all of the oils, margarines and spread products of the invention are expected to conform to whatever limits are imposed by governmental authorities.

The limit of detection for trans isomers of fatty acids in oils is around 0.1%. (The gas chromatography method for detecting trans fatty acids in oils is outlined in AOCS Ce 1C-89). Reports of "low trans isomer oils" produced by modifications of the hydrogenation method can achieve levels of 5-20% (w/w), but usually at the cost of high saturated fatty acid levels (Allen, D. A. (1998) *Lipid Technology*, 10(2), 29–33). It is believed that the oils, fat products, and blended fat products, that are wholly or partially non-hydrogenated and non-chemically modified, in the instant invention, should be substantially free of trans fatty acids, i.e., they should achieve trans fatty acid concentrations of below 20% (w/w), preferably below 10%, more preferably below 5%, even more preferably below 3%, and again more preferably below 1%, and most preferably below 0.5% of the oil.

Interesterification refers to the exchange of the fatty acyl moiety between an ester and an acid (acidolysis), an ester and an alcohol (alcoholysis) or an ester and ester (transesterification). Interesterification reactions are achieved using chemical or enzymatic processes. Random or directed transesterification processes rearrange the fatty acids on the triglyceride molecule without changing the fatty acid composition. The modified triglyceride structure may result in a fat with altered physical properties. Directed interesterfication reactions using lipases are becoming of increasing interest for high value specialty products like cocoa butter substitutes. Products being commercially produced using interesterification reactions include but are not limited to shortenings, margarines, cocoa butter substitutes and structured lipids containing medium chain fatty acids and polyunsaturated fatty acids. Interesterification is further discussed in Hui, Y. H., 1996, Bailey's Industrial Oil and Fat Products, Volume 4, John Wiley & Sons.

Fatty acids and fatty acid methyl esters are two of the more important oleochemicals derived from vegetables oils. Fatty acids are used for the production of many products such as soaps, medium chain triglycerides, polyol esters, alkanolamides, etc. Vegetable oils can be hydrolyzed or split into their corresponding fatty acids and glycerine. Fatty acids produced from various fat splitting processes may be used crude or more often are purified into fractions or individual fatty acids by distillation and fractionation. Purified fatty acids and fractions thereof are converted into a wide variety of oleochemicals, such as dimer and trimer acids, diacids, alcohols, amines, amides, and esters. Fatty acid methyl esters are increasingly replacing fatty acids as starting materials for many oleochemicals such as fatty alcohols, alkanolamides, a-sulfonated methyl esters, diesel oil components, etc. Glycerine is also obtained by the cleavage of triglycerides using splitting or hydrolysis of vegetable oils. Further references on the commercial use of fatty acids and oleochemicals may be found in Erickson, D. R., 1995, Practical Handbook of Soybean Processing and Utilization, The American Oil Chemists' Society, and United Soybean Board; Pryde, E. H., 1979, Fatty Acids, The American Oil Chemists' Society; and Hui, Y. H., 1996, Bailey's Industrial Oil and Fat Products, Volume 4, John Wiley & Sons.

Those skilled in the art will appreciate that products obtained from the hydrogenation, fractionation, interesterification or hydrolysis of the oils described in the instant invention can be used to make a margarine or spread product. Furthermore, blended products can be made as described below utilizing fractionated or unfractionated oils of the invention, either in their natural state or modified by hydrogenation, fractionation, interesterification and/or hydrolysis, in combination with other ingredients to produce a margarine or spread product.

Margarine is a flavored food product, commonly used as a dairy butter substitute for table or cooking purposes such as flying, baking, etc. The composition of margarine is typically 80% fat, made by blending selected fats and oils with other ingredients and fortified with Vitamin A. Examples of ingredients that can be used to make a blended fat include, but are not limited to, at least one component selected from the group consisting of fully hydrogenated soybean oil, fully hydrogenated cottonseed oil, fully hydrogenated palm oil, partially hydrogenated soybean oil, partially hydrogenated cottonseed oil, partially hydrogenated palm oil, soybean oil, corn oil, palm oil, canola oil, sunflower oil, peanut oil, safflower oil or mixtures thereof.

The process of blending, and the ultimate product, can be varied for different applications. All products containing less than 80% fat require labeling as "spreads". The terms "spread" or "spread products" are used interchangeably herein. Margarine and spreads may contain one or more aqueous-phase ingredients, as well as other optional ingredients with specific functions. There are over 10 different types of margarine and spreads produced today including regular, whipped, soft-tub, liquid, diet, spreads, no-fat, restaurant, bakers, and specialty types that are all packaged as different products.

In the early 1950's almost all consumer margarine was a stick variety. Sales and per capita consumption rose and surpassed that of butter in 1957. Sales increases stimulated new technological progress and new product development. Spreadable margarine, polyunsaturated margarine, and low-fat products were developed to satisfy the desire for convenience and nutritional awareness, and weight consciousness of the consumer.

The first major departure from the past was the introduction of soft margarine spreadable from the refrigerator and packaged in tubs. This soft, fill-fat product captured one-fourth of the margarine market by 1973. In recent years, stick table spreads account for slightly less than half of the total table spread market. The most significant recent trend is away from margarine (80%) fat to spreads containing lower fat levels. Originally introduced at 60% fat, since 1980 spread containing from 75% to less than 5% fat have appeared in the marketplace. The products are sold in stick, liquid, and soft whipped forms. Low calorie, soft and stick spreads containing 40–75% fat are usually formulated from the same oil blends as those used for the manufacture of soft and stick margarines, respectively. A detailed description of margarine and spread manufacturing practices and product characteristics can be found in Bailey's Industrial Oil and Fat Products, Fifth Edition, Volume 3, Y. H. Hui, Ed., John Wiley & Sons, Inc, New York, 1996, pp 65–114; and Bailey's Industrial Oil and Fat Products, Fifth Edition, Volume 4, Y. H. Hui, Ed., John Wiley & Sons, Inc, New York, 1996, pp 491–568.

Consumer margarines are formulated by blending two or more oil basestocks with different degrees of hardness. This permits the margarines to be spreadable directly out of the refrigerator and to maintain a solid consistency at room temperature. The properties of a good performing margarine can be profiled by measuring the Solid Fat Content (SFC, see below) of the fat blend. This profile can then be used to predict the performance of other oil blends as margarine products. A detailed description of margarine formulation can be found in: Fats and Oils, Formulation and Processing for Applications, ed. R. D. O'Brien, Technomic Publishing Co, Lancaster, Pa., 1998, pp 437–457.

The melting characteristics and plasticity of a fat can be measured by industry standard techniques. The most commonly used methods are Solid Fat Index (SFI AOCS Cd10-57-93) and Solid Fat Content (SFC, AOCS Cd16b-93(97)). SFI determinations are based on dilatometry which measures the amount of solid or liquid in a fat based on volumetric changes resulting from a fat melting to the liquid state. This technique is gradually being replaced by SFC. This method is based on pulsed, low resolution nuclear magnetic resonance (NMR) to measure the relative amounts of solid and liquid in a sample based on the difference in the rates of relaxation of protons in the two phases after the sample has been pulsed. Conversion of SFI to SFC data has not always been reliable. For a given sample, the percentage of solids is measured across temperatures generally ranging between 10° and 40° C. The entire SFC curve is required in order to understand the properties of the fat at different temperatures. The functionality of the fat is based on both the solids content and on the slope of the SFC curve at critical temperatures, for example, between room and body temperature. In this way, the plasticity of that fat can be predicted for temperatures critical to performance.

For margarine or conventional oils and fats, SFC is determined using the direct serial, non-stabilizing method. The SFC NMR direct method measures and compares signals from the solid and liquid phases. SFC is defined as the percent ratio between the NMR response obtained from the hydrogen nuclei in the solid phase versus the response from nuclei in both the solid and the liquid phases of the sample. The serial, non-stabilizing method utilizes a single set of samples that are tempered by melting and storage at 100° C. for 15 minutes, holding at 60° C. for 5 minutes, and at 0° C. for 1 hour. The samples are then held at each recording temperature for 30 minutes and moved to the next higher temperature immediately after determination of SFC. It is believed that high stearic with high oleic oils presented here, as well as those oils with similar compositions, will be capable of producing fat products with SFC profiles of less than 20 at 25° C., preferably less than 15 at 25° C., more preferably less than 10 at 25° C., and most preferably less than 5 at 25° C., and greater than 20 at 10° C., preferably between 20 and 50 at 10° C., and most preferably between 20 and 35 at 10° C.

The melting point of a fat is also an important measurement. Since fats are made up of a mixture of triglycerides which have different melting points, a sharp determination is not always possible. There are several methods common to the industry which measure melting point including capillary melting point (AOCS Cc1-25-93), Wiley melting point (AOCS Cc2-38-91), slip point (AOCS Cc3-25-93), and dropping point (AOCS Cc18-80-95).

Typical solid fat index values of US margarine oils are given in Table 3. The numbers are representative of commercial products. For a given type of margarine, however, specifications may vary considerably been manufacturers depending on: 1) the organoleptic characteristics desired, 2) compositional requirements to meet nutrient content claims or other information on the nutrition panel, 3) whether the product will be marketed using unrefrigerated display, and 4) the type of packaging equipment available. The solids values are indicative of finished product spreadability at refrigerator temperatures (10° C.), resistance to oil-off at room temperature (21.1° C.), and melt in the mouth qualities (33.3° C.).

TABLE 3

Typical Solid Fat Indices of U.S. Table Spreads
Solid Fat Index

|  | 10° | 21.1° | 26.7° | 33.3° | 37.7° |
|---|---|---|---|---|---|
| Stick | 28 | 16 | 10 | 2 | 0 |
| Soft stick | 20 | 13 | 9 | 2.5 | 0 |
| Soft tub | 11 | 7 | 5 | 2 | 0.5 |
| Liquid | 3 | 2.5 | 2.5 | 2 | 1.5 |
| Butter | 32 | 12 | 7 | 2 | 0 |

The physical and functional aspects of a margarine product are primarily dependent upon the characteristics of its oil phase. A direct relationship exists between the fat solids content and the structure, consistency, and plasticity of the finished margarine. Margarine consistency, flavor and emulsion stability depends upon crystallized fat. In the United States, hydrogenation is the preferred process for changing the solids/liquid relationship of margarine basestocks. However, hydrogenated oils have become controversial due to the presence of trans fatty acid isomers that result from the hydrogenation process. Ingestion of large amounts of trans isomers has been linked with detrimental health effects including increased ratios of low density to high density lipoproteins in the blood plasma and increased risk of coronary heart disease. From an environmental standpoint, the use of metal catalysts in the hydrogenation process has raised issues regarding the reclamation and disposal of a toxic metal waste product. Increased public awareness of the negative aspects of hydrogenation will likely lead to significant changes in margarine formulation to reduce or eliminate the presence of industrially-modified oils.

A number of methods are well known to those skilled in the art for determining oxidative stability. A standard method now commonly used to evaluate the stability of commercial cooking oils is the Oxidative Stability Index (OSI) which is measured automatically using a machine manufactured by Ominion, Inc. of Rockland, Mass., USA.

The OSI machine work by bubbling air through oil heated to 110° C. As the oil oxidizes, volatile organic acids, primarily formic acid, is formed which can be collected in distilled water in a cell. The machine constantly measure the conductivity of the distilled water and the induction period is determined as the time it takes for this conductivity to begin a rapid rise. It is believed that the high stearic with high oleic oils presented in the invention, in their unblended and blended forms, as well as those oils with similar compositions, will be capable of producing fat products with OSI(110) greater than 15, preferably greater than 25, and most preferably greater than 35.

EXAMPLES

The following Examples are intended to illustrate the present invention and do not constitute a limitation thereon. All temperatures are given in Celsius unless indicated otherwise. Solid Fat Content (SFC) profiles listed in these Examples report the percentage of the total fat moieties that were determined to be in the solid phase at the indicated temperature.

Example 1

Preparation of Oils from Soybeans and Analyses of Fatty Acid Compositions

All of the oils used in these examples were prepared according to the following laboratory scale method. Harvested soybeans were heated in the microwave to 180° F., cooled to room temperature and cracked using a Roskamp TRC 650-6 Crack and Roll. Soybean hulls were removed using a Kice Aspirator and the remaining meats were heated to 180° F. and flaked in a Roskamp TRC 912 Flake and Roll. Crude oil was extracted in a glass, water-jacketed extraction vessel heated to 60° for 45 minutes using a solvent to solids ratio of approximately 4:1. The hexane/oil miscella was collected and the extraction repeated. The miscella was desolventized using a rotary evaporator leaving crude oil.

A volume of an 85% phosphoric acid solution equal to 0.1% (v/v) of the crude oil was added and the solution heated to 65°–70° for 10 minutes while stirring. Warm (60°) NaOH (8% aqueous solution) was added dropwise to the oil to neutralize the free fatty acids and the $H_3PO_4$ with an additional 0.2% wt/wt excess. The solution was stirred for five minutes and the solids separated by centrifugation. The oil was water washed by adding hot water to 20% (v/v) as the sample was heated to 90° with rapid agitation. The oil and water were allowed to cool at room temperature for 10 minutes and then separated by centrifugation. The oil was dehydrated using very rapid agitation under vacuum at 85°–95° for 30 minutes or until all moisture (bubbles, condensation) had been removed. The vacuum was then broken with nitrogen. The oil was bleached by adding 2% (wt/wt) Activated Bleaching Earth (AOCS #Z1077) and the solution mixed under vacuum for 30 minutes at 85°–95° before cooling to 80°. The vacuum was broken with nitrogen and 1% (wt/wt) of diatomaceous earth was added and the mixture filtered through a prepared bed of diatomaceous earth.

Citric acid was added to approximately 50 ppm, and the oil was deodorized at 240° with steam (4 mL water per 100 g oil) in a glass deodorizer for approximately 1 hour. The oil was cooled to 80° with sparging, and it was further cooled to 40° under nitrogen. The refined, bleached, and deodorized oil was stored frozen under a nitrogen atmosphere.

All of the fatty acid composition analyses described in these examples were determined essentially by the methods described in AOCS Ce 1c-89. Fatty acid methyl esters were prepared as follows. Ten µL oil or liquefied fat was mixed with 1 mL hexane and 0.25 mL of a 3% sodium methoxide solution for 30 minutes. Acetic acid (0.1 mL of a 10% solution) was added, the sample was mixed and the layers separated by centrifugation. The resulting fatty acid methyl esters extracted in the hexane layer were resolved by gas chromatography (GC). Hewlett Packard 5890GC (Wilmington, Del.) equipped with a SP2340 column (60 m, 0.25 mm ID, 0.20 micron film thickness) (Supelco, Bellefonte, Pa.). Column temperature was 150° at injection and the temperature programmed from 150° to 200° at 2° C./min over 40 minutes. Injector and detector temperatures were 215° and 230°, respectively. All compositional values reported are relative values calculated from the integrated areas measured by the GC detector.

All of the SFC determinations were done essentially by the methods described in AOCS Cd16b-93.

All of the oxidative stability measurements were determined by OSI essentially by the methods described in AOCS Cd12b-92(93).

Example 2

Solid Fat Content of Commercial Margarine

Samples of commercial margarine with varying degrees of solidity were analyzed for SFC. Samples were prepared by melting the product at 100 degrees and removing the aqueous layer. The resulting fat fraction was analyzed for SFC as a function of temperature and the results are listed in Table 4. The table shows the range of solids which can be used to produce different types of margarine and spread products depending on the fat plasticity and the product form desired (e.g., soft tub, stick, low fat spread).

and the resulting progeny was crossed to a wild-type line, A2506 to produce L9216116-109). The seeds produced have a higher stearic acid content and lower linolenic acid content than conventional soybeans. The parents HST1, HO2, and HO4 (see Table 2) are mutant lines selected by the mutagenesis protocols outlined in U.S. Pat. No. 5,710,365, except different soybean lines were used as starting materials for the mutagenesis, and selection was based on variation in fatty acid content instead of carbohydrate content. HST1 is a mutant of line N85-2176 which is a high oleic, low linolenic line developed at North Carolina State University by J. W. Burton (Kuhr et al., Mar. 26, 1987 Release Notice for N85-2124, N85-2131, and N85-2176. USDA Agric Res. Services). HST1 differs from its parent N85-2176 by virtue of its abnormally high stearic acid content (HST=high stearic), while retaining the lower linolenic acid content of N85-2176. The high stearic mutation in HST1 suppresses (is epistatic to) the high oleic gene(s) that are present in the genetic background from N85-2176. Therefore, HST1 is not high in oleic acid like N85-2176. The stearic mutation in HST1 is allelic to fasa (see Table 2) in line A6 (W. Fehr from Iowa State) and results in a similar phenotype when crossed into similar backgrounds as the fasa allele. Crosses between N85-2176 and A5 (W. Fehr from Iowa State) confirm that N85-2176 contains an allele of the fan gene (see Table 2) present in A5 that confers a similar low linolenic phenotype. Therefore, HST1 contains both a high stearic mutation (allelic to fasa) and a low linolenic mutation (allelic to fan).

HO2 is a DuPont proprietary mutant line selected from mutagenesis of the line N83-2176. The mutagenesis protocol was essentially the same as the one described in U.S. Pat. No. 5,710,365, except that N85-2176 was used as the starting material for mutagenesis, and selection was based upon variation in fatty acid content instead of carbohydrate content. HO2 differs from N85-2176 (fan) in that it has a slightly higher oleic acid content (HO=high oleic), but retains the low linolenic acid content of N85-2176. Therefore, HO2 contains an unnamed mutation that confers higher oleic acid content than N85-2176 in addition to the fan gene.

TABLE 4

Solid fat content of commercial margarine at various temperatures

| Functionality | Product Form | 10 | 15 | 20 | 25 | 30 | 35 | 40 |
|---|---|---|---|---|---|---|---|---|
| 68% vegetable oil spread | stick | 24.2 | 23.5 | 16.2 | 8.5 | 4.1 | 0.9 | 0.5 |
| 40% vegetable oil spread | stick | 22.2 | 21.7 | 15 | 8 | 3.6 | 1.1 | 0.0 |
| 70% corn oil spread | stick | 31.0 | 25.8 | 17.6 | 10.9 | 5 | 0.7 | 0.1 |
| 40% vegetable oil spread | soft tub | 16.4 | 11.9 | 7.2 | 4.1 | 1.7 | 0.6 | 0.3 |
| 24% vegetable oil spread | soft tub | 18.5 | 13.9 | 9.4 | 5.8 | 3.3 | 1.3 | 0.6 |
| 70% vegetable oil spread | stick | 40.3 | 32.1 | 22.7 | 12.6 | 5.1 | 1.3 | 0.1 |
| corn oil margarine | stick | 35.7 | nd | 22.1 | 13.8 | 6.7 | 1 | nd |
| soybean oil margarine | stick | 36.5 | nd | 23 | 15.4 | 8.9 | 3 | nd |
| soft margarine | soft tub | 19.1 | nd | 9 | 4.4 | 1.5 | −0.1 | nd |
| butter | stick | 47.3 | 34.9 | 20 | 11.8 | 5.1 | 1.2 | 0.0 |

Example 3

Solid Fat Content of a High Stearic Soybean Oils

High stearic acid soybeans from the line designated L9216116-109 were developed at DuPont from a pedigree (HST1*(HO2*HO4))*A2506 (which means the progeny from a cross between HO2 and HO4, was crossed to HST1, HO4 is a DuPont proprietary mutant line selected from mutagenesis of the line A5. The mutagenesis protocol was essentially the same as the one described in U.S. Pat. No. 5,710,365, except that A5 was used as the starting material for the mutagenesis, and selection was based upon variation in fatty acid content instead of carbohydrate content. HO4 differs from A5 (fan) in that it has a higher oleic acid content (HO=high oleic), but retains the low linolenic acid content of A5. Therefore, HO4 contains an unnamed mutation that confers higher oleic acid content than A5 in addition to the fan gene.

It is believed that a derivative of A6 (fasa), or similar plant yielding seeds with an oil composition comprising a high stearic and low linolenic acid phenotype similar to that disclosed in the instant invention, would be useful for the methods described herein.

High stearic and high oleic acid soybeans were developed as outlined in Example 5.

All soybean oils were prepared as described in Example 1 and analyzed for fatty acid composition and solid fat content at a variety of temperatures.

Tables 5 and 6 show the compositional and functional characteristics of high stearic soybean oils ranging from 15% to 22% stearic acid. In addition, four of the oils have elevated levels of oleic acid. The oil containing 22% stearic acid and a normal oleic content did not have enough solidity to meet the specifications required for a soft tub margarine (see FIG. 1). However, the SFC profile of the 22% stearic acid, high oleic acid combination fell within the ranges published for commercial soft tub margarine. It is believed that high stearic combined with high oleic oils presented here, as well as those oils with similar compositions, will be capable of producing fat products with SFC profiles of less than 20 at 25° C., preferably less than 15 at 25° C., more preferably less than 10 at 25° C., and most preferably less than 5 at 25° C., and greater than 20 at 10° C., preferably between 20 and 50 at 10° C., and most preferably between 20 and 35 at 10° C.

Oils with less than 22% stearic acid did not have an SFC profile consistent with margarine and spread products. Therefore, SFC profiles consistent with margarine and spread products could be obtained from unblended oils with high oleic acid concentrations combined with stearic acid concentrations of at least 22%.

TABLE 5

Fatty acid composition

| Chain length: unsaturation | 16:0 | 18:0 | 18:1 | 18:2 | 18:3 | 20:0 |
|---|---|---|---|---|---|---|
| high stearic | 8.8 | 22.2 | 14.6 | 48.1 | 4.9 | 1.5 |
| high stearic/high oleic oil A | 5.9 | 21.9 | 62.8 | 2.6 | 3.6 | 1.8 |
| high stearic/high oleic oil B | 6.0 | 18.6 | 66.8 | 2.3 | 3.6 | 1.5 |
| high stearic/high oleic oil C | 5.5 | 17.6 | 67.6 | 3.4 | 3.7 | 1.4 |
| high stearic/high oleic oil D | 5.9 | 15.1 | 69.2 | 2.6 | 3.6 | 1.2 |

TABLE 6

Percent SFC as a function of temperature

| Temperature | 10° | 15° | 20° | 25° | 30° | 35° | 40° |
|---|---|---|---|---|---|---|---|
| high stearic | 13.9 | 6.8 | 4.6 | 0.1 | 0.4 | 0 | 0 |
| high stearic/high oleic oil A | 21.2 | 16.4 | 7.1 | 4.5 | 0 | 0 | 0 |
| high stearic/high oleic oil B | 29.9 | 19.8 | 4.3 | 3.1 | 0.3 | 0.6 | 0.5 |
| high stearic/high oleic oil C | 28.4 | 17.6 | 2.9 | 1.4 | 0.5 | 0 | 0.3 |
| high stearic/high oleic oil D | 23.6 | 11.5 | 1.0 | 0.7 | 0.2 | 0.4 | 0.3 |

Example 4

Base Oil Blend to Produce a Margarine Lacking Trans Fatty Acid Isomers

Figure 2:
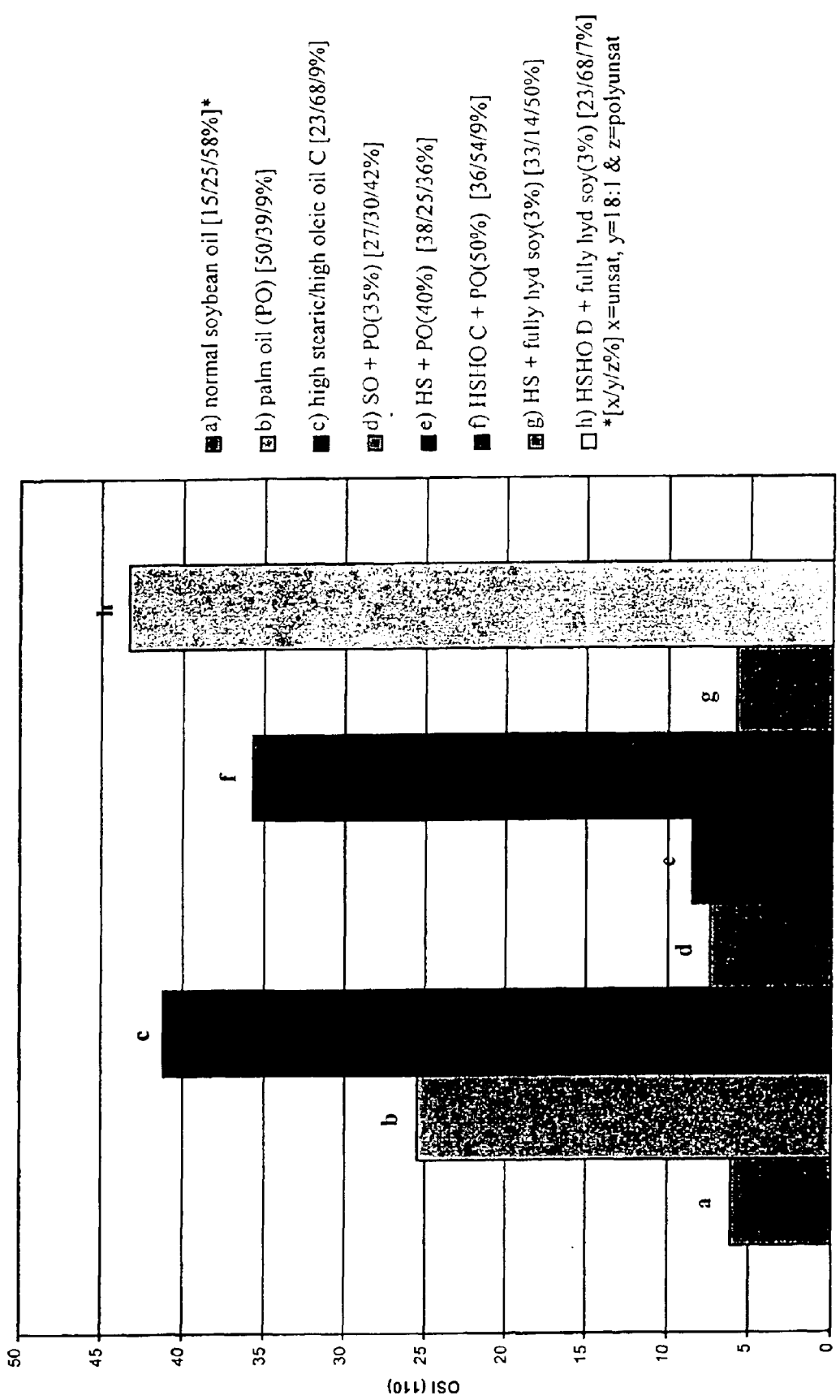
Figure 3:
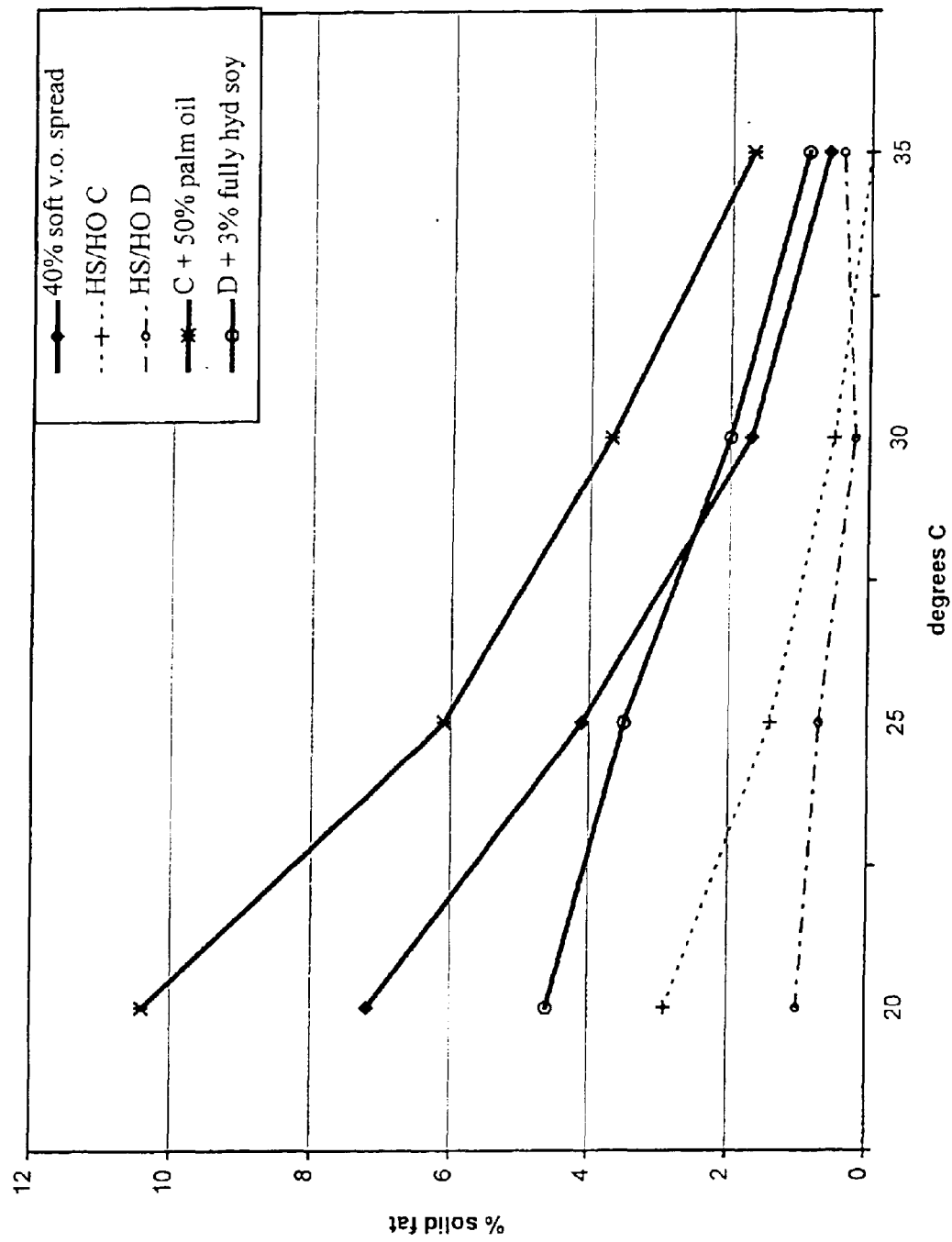
FIG. 3 shows that blending high stearic and high oleic acid oils (HS/HO C and HS/HO D), with hardstocks such as palm oil or fully hydrogenated soybean oils, improves their SFC profiles to conform with the characteristics of a vegetable oil spread.

High stearic oils were blended (as indicated in Table 7) with either palm oil or fully hydrogenated soybean flakes (Dritex PST Hydrogenated Soybean Flakes, AC HUMKO, 525 W. 1$^{st}$ Avenue, Columbus, Ohio) to produce fats that met the SFC requirements for a margarine and would not contain trans fatty acid isomers. The resulting blends were analyzed for fatty acid composition, solid fat content at a variety of temperatures, and oxidative stability. Table 7 shows the fatty acid compositions and OSI values of each of these blends. A graphical representation is shown in FIG. 2. Blends made from high stearic/high oleic oils show oxidative stability values 4–7 fold greater than blends made from high stearic oils with normal oleic levels. It is believed that the high stearic with high oleic oils presented here, in their unblended and blended forms, as well as those oils with similar compositions, will be capable of producing fat products with OSI(110) greater than 15, preferably greater than 25, and most preferably greater than 35. Table 8 shows the solid fat content for each of these blends. The blended forms of high stearic/high oleic oils demonstrating high oxidative stability (HSHO C+palm oil, and HSHO D+fully hydrogenated soybean oil) have also improved their SFC profiles as shown in FIG. 3, and now conform with the curve for soft-tub margarine. It is believed that high stearic with high oleic oils presented here, in their unblended and blended forms, as well as those oils with similar compositions, will be capable of producing fat products with SFC profiles of less than 20 at 25° C., preferably less than 15 at 25° C., more preferably less than 10 at 25° C. most preferably less than 5 at 25° C., and greater than 20 at 10° C., preferably between 20 and 50 at 10° C., and most preferably between 20 and 35 at 10° C.

TABLE 7

Fatty acid composition of blended oils (%)

| | 14:0 | 16:0 | 18:0 | 18:1 | 18:2 | 18:3 | 20:0 | OSI (110) |
|---|---|---|---|---|---|---|---|---|
| high stearic/high oleic oil C | nd | 5.5 | 17.6 | 67.6 | 3.4 | 3.7 | 1.4 | 41.2 |
| high stearic/high oleic oil D | | 5.9 | 15.1 | 69.2 | 2.6 | 3.6 | 1.2 | nd |
| palm oil | 1.2 | 44.7 | 4.5 | 39.0 | 8.6 | 0.1 | 0.4 | 25.5 |
| fully hydrogenated soybean oil (FHS) | 1.3 | 55.2 | 41.2 | 0.3 | 0.1 | 0 | 0.5 | nd |
| normal soybean oil | 0.1 | 10.9 | 4.0 | 24.6 | 51.4 | 6.7 | 0.3 | 6.1 |
| blend of HSHO oil C + palm oil (50%) | 0.6 | 24.0 | 11.0 | 53.8 | 6.5 | 1.9 | 0.9 | 35.7 |
| blend of high stearic + palm oil (40%) | 0.4 | 22.2 | 15.1 | 24.6 | 32.4 | 2.6 | 1.0 | 8.5 |

TABLE 7-continued

Fatty acid composition of blended oils (%)

|  | 14:0 | 16:0 | 18:0 | 18:1 | 18:2 | 18:3 | 20:0 | OSI (110) |
|---|---|---|---|---|---|---|---|---|
| blend of HSHO oil D + FHS (3%) | nd | 7.3 | 15.8 | 68.2 | 2.8 | 3.4 | 1.1 | 43.3 |
| blend of high stearic + FHS (3%) | 0.1 | 10.3 | 22.4 | 14.2 | 45.6 | 4.0 | 1.4 | 5.8 |
| normal soybean + palm oil (35%) | 0.4 | 22.1 | 4.1 | 30.1 | 36.7 | 4.5 | 0.3 | 7.4 |

TABLE 8

SFC as a function of temperature

| Temperature | 10° | 20° | 25° | 30° | 35° |
|---|---|---|---|---|---|
| high stearic/high oleic oil C | 28.4 | 2.9 | 1.4 | 0.5 | 0 |
| high stearic/high oleic oil D | 24.2 | 1.8 | 0.6 | 0 | 0 |
| palm oil | 57.2 | 31.6 | 19.7 | 10.9 | 5.0 |
| blend of HSHO oil C + palm oil (50%) | 25.8 | 10.4 | 6.1 | 3.7 | 1.7 |
| blend of high stearic + palm oil (40%) | 22.7 | 7.4 | 4.8 | 2.5 | 0.7 |
| blend of HSHO oil D + FHS (3%) | 24.4 | 4.6 | 3.5 | 2.0 | 0.9 |
| blend of high stearic + FHS (3%) | 17.3 | 8.2 | 3.6 | 2.3 | 1.2 |
| normal soybean + palm oil (35%) | 12.8 | 6.3 | 4.2 | 3.3 | 1.5 |

Example 5

Soybeans with High Stearic and High Oleic Content

Crosses were performed between a soybean line which has elevated levels of oleic acid in its seed fatty acids and a line which has elevated levels of stearic acid in its seed fatty acids. The high oleic line contains a transgene copy of the soybean fatty acid desaturase gene, gmFAD2-1 (Heppard, E. P. et al. (1996) *Plant Physiol.* 110:311–319), that results in co-suppression and therefore down regulation of the gmFAD2-1 message level and is described in WO 97/40698. Decreased expression of the FAD2-1 function leads to a decrease in activity of delta-12 desaturase, and a decrease in the accumulation of poly-unsaturated fatty acids. The high oleic line is designated D2T and the typical fatty acid profile of its seed lipid is given in Table 2. The high stearate parent is a fatty acid synthesis mutant isolated from a mutagenized soybean seed population (U.S. Pat. No. 5,557,037), designated A6, and containing a fatty acid mutant fasa allele. Its typical seed lipid fatty acid profile is given in Table 2.

F1 seeds obtained from the crosses were planted to obtain F1 plants. The F1 plants were then self-pollinated to obtain F2 seeds that were segregating for both of the loci affecting the seed fatty acid profile. These F2 seeds were planted and the plants were self-pollinated as in the previous generation. The relative content of the five main fatty acids in bulked seed samples from individual F2 plants was determined by gas liquid chromatography as described in WO 94/11516. Remaining seed from F2 plants containing maximum stearic and oleic acid content were selected, planted and allowed to self pollinate in order to obtain F3:4 seed. A sample of F4 seed from each F3 plant (F3:4 seed) was then submitted for GC analysis so that individual F3:4 phenotypes could be determined. F3:4 plant phenotypes tracing back to a common F2 plant ancestor were then averaged to obtain mean phenotypes for F2-derived families (F2:4 family means). Single plants and family means that were highest in oleic and stearic acid are shown in Table 9. The individual plant lines and the family means are presented in order of decreasing stearic acid in the seed fatty acids.

TABLE 9

Seed fatty acid profiles from individual plants and F2:4 family means arising from a cross of the high oleic parent D2T and the high stearic parent fasa

| | Individual Fatty Acid Content (% of total seed fatty acid) | | | | | |
|---|---|---|---|---|---|---|
| Line ID | 16:0 | 18:0 | 18:1 | 18:2 | 18:3 | generation and type |
| 7SO-2334-1 | 7 | 26 | 61 | 1 | 3 | F3:4 single plant |
| 7SO-2293-2 | 6 | 26 | 61 | 2 | 3 | F3:4 single plant |
| 7SO-2293-1 | 6 | 25 | 62 | 2 | 3 | F3:4 single plant |
| 7SO-2303-5 | 6 | 24 | 66 | 0 | 2 | F3:4 single plant |
| 7SO-2339-1 | 6 | 24 | 64 | 1 | 3 | F3:4 single plant |
| 7SO-2295-1 | 6 | 24 | 64 | 1 | 3 | F3:4 single plant |
| 7SO-2331-3 | 7 | 24 | 63 | 1 | 3 | F3:4 single plant |
| 7SO-5097-3 | 6 | 20 | 67 | 2 | 3 | F3:4 single plant |
| 7SO-5097-1 | 6 | 20 | 66 | 2 | 3 | F3:4 single plant |
| 7SO-2356-1 | 6 | 18 | 72 | 0 | 3 | F3:4 single plant |
| 7SO-2306-2 | 6 | 18 | 71 | 2 | 3 | F3:4 single plant |
| 7SO-2305-3 | 6 | 18 | 70 | 2 | 2 | F3:4 single plant |
| 7SO-2310-3 | 6 | 18 | 70 | 2 | 3 | F3:4 single plant |
| 7SO-2293 | 6 | 24 | 63 | 2 | 3 | F2:4 family mean of 9 plants |
| 7SO-2334 | 6 | 23 | 65 | 1 | 3 | F2:4 family mean of 8 plants |
| 7SO-2339 | 6 | 23 | 65 | 1 | 3 | F2:4 family mean of 7 plants |
| 7SO-2379 | 6 | 19 | 70 | 1 | 2 | F2:4 family mean of 3 plants |
| 7SO-2305 | 6 | 18 | 71 | 2 | 3 | F2:4 family mean of 10 plants |

The very low poly-unsaturated fatty acid phenotype arising from the D2T parent is maintained in selected progeny from the cross as is the very high level of stearic acid coming from the fasa containing parent. The increased level of stearic acid in the selected progeny from the cross relative to the D2T parent causes a decrease in the oleic acid content.

Example 6

Soybeans with High Oleic Acid and High Palmitic Acid and High Stearic Acid Content Crosses were made between soybean lines contain the D2T gene (for high oleic acid content) and soybean lines containing both a fap2 allele (for high palmitic acid content) and a fasa allele (for high stearic acid content) to obtain F1 progeny. F1 progeny were then selfed in subsequent generations to obtain F2 seeds and F2:3 families. F2:3 families containing maximum palmitic+stearic+oleic acid content were selected and planted and allowed to self pollinate in order to obtain F3:4 seed. A sample of F4 seed from each F3 plant (F3:4 seed) was then submitted for GC analysis so that individual F3:4 phenotypes could be determined. F3:4 plant phenotypes tracing back to a common F2 plant ancestor were then averaged to obtain mean phenotypes for F2-derived families (F2:4 family means). Single plants and family means that were highest in palmitic+stearic+oleic acid content are shown in Table 10, and are presented in order of decreasing total seed saturated fatty acids.

TABLE 10

Individual Plant and Family Mean Phenotypes With a Combination of High Oleic Acid and High Plamitic Acid and High Stearic Acid Content

| Line ID | Individual Fatty Acid Content (% of total seed fatty acid) | | | | | generation and type |
|---|---|---|---|---|---|---|
| | 16:0 | 18:0 | 18:1 | 18:2 | 18:3 | |
| 7HSO-5076-5 | 12 | 21 | 58 | 3 | 3 | F3:4 single plant |
| 7HSO-2201-2 | 12 | 19 | 62 | 2 | 3 | F3:4 single plant |
| 7HSO-2229-1 | 12 | 18 | 65 | 1 | 3 | F3:4 single plant |
| 7HSO-2201-1 | 11 | 19 | 62 | 2 | 3 | F3:4 single plant |
| 7HSO-2227-5 | 11 | 18 | 66 | 1 | 3 | F3:4 single plant |
| 7HSO-2207-5 | 11 | 18 | 65 | 1 | 3 | F3:4 single plant |
| 7HSO-5074-3 | 11 | 17 | 63 | 1 | 3 | F3:4 single plant |
| 7HSO-2201-0 | 11 | 18 | 63 | 2 | 3 | F2:4 family mean of 3 plants |
| 7HSO-2208-0 | 11 | 16 | 68 | 1 | 3 | F2:4 family mean of 3 plants |
| 7HSO-2228-0 | 11 | 16 | 68 | 1 | 3 | F2:4 family mean of 4 plants |
| 7HSO-2207-0 | 11 | 15 | 68 | 1 | 3 | F2:4 family mean of 6 plants |

Example 7

Soybeans with High Oleic Acid and Low Palmitic Acid Content

Crosses were made between soybean lines containing the D2T gene (for high oleic acid content) and soybean lines containing both a fap1 allele and a fap3 allele (for low palmitic acid content) to obtain F1 progeny. F1 progeny were then selfed in subsequent generations to obtain F2 seeds and F2:3 families. F2:3 families containing both minimum palmitic acid content and maximum oleic acid content were then selected and planted and allowed to self pollinate in order to obtain F3:4 progenies. A sample of F4 seed from each F3 plant (F3:4 seed) was then submitted for GC analysis so that individual F3:4 phenotypes could be determined. F3:4 plant phenotypes tracing back to a common F2 plant ancestor were then averaged to obtain mean phenotypes for F2-derived families (F2:4 family means). Single plants and family means that were both lowest in palmitic acid content and highest in oleic acid content are shown in Table 11, and are presented in order of increasing palmitic acid in total seed fatty acids. Since selection for low palmitic acid content requires precision to a tenth of a percent, palmitic values in Table 11 are shown to that level of precision while values for the other fatty acids are rounded to the nearest whole percent.

TABLE 11

Individual Plants and F2:4 Family Mean Phenotypes With a Combination of High Oleic and Low Palmitic Acid Content (D2T + fap1 + fap3 genes)

| Line ID | Individual Fatty Acid Content (% of total seed fatty acid) | | | | | generation and type |
|---|---|---|---|---|---|---|
| | 16:0 | 18:0 | 18:1 | 18:2 | 18:3 | |
| 7AO-2079-12 | 2.7 | 3 | 89 | 1 | 3 | F3:4 single plant |
| 7AO-2083-1 | 2.8 | 3 | 90 | 1 | 2 | F3:4 single plant |
| 7AO-2072-4 | 2.9 | 3 | 89 | 1 | 2 | F3:4 single plant |
| 7AO-2065-1 | 2.9 | 3 | 89 | 1 | 3 | F3:4 single plant |
| 7AO-2083-3 | 3.0 | 3 | 89 | 1 | 2 | F3:4 single plant |
| 7AO-2075-3 | 3.0 | 3 | 89 | 1 | 3 | F3:4 single plant |
| 7AO-2079-1 | 3.0 | 3 | 88 | 2 | 3 | F3:4 single plant |
| 7AO-2072-1 | 3.1 | 3 | 88 | 1 | 3 | F3:4 single plant |
| 7AO-2085-5 | 3.2 | 3 | 89 | 1 | 2 | F3:4 single plant |
| 7AO-2084-1 | 3.2 | 3 | 88 | 2 | 2 | F3:4 single plant |
| 7AO-2072-6 | 3.2 | 3 | 88 | 1 | 3 | F3:4 single plant |
| 7AO-2081-6 | 3.3 | 3 | 90 | 1 | 2 | F3:4 single plant |
| 7AO-2074-7 | 3.3 | 3 | 89 | 1 | 3 | F3:4 single plant |
| 7AO-2081-3 | 3.4 | 3 | 89 | 1 | 2 | F3:4 single plant |
| 7AO-2087-1 | 3.4 | 3 | 88 | 3 | 3 | F3:4 single plant |
| 7AO-2072-0 | 3.0 | 3 | 89 | 1 | 3 | F2:4 family mean of 6 plants |
| 7AO-2083-0 | 3.5 | 3 | 89 | 1 | 2 | F2:4 family mean of 4 plants |
| 7AO-2074-0 | 3.5 | 3 | 88 | 1 | 3 | F2:4 family mean of 7 plants |
| 7AO-2080-0 | 3.6 | 3 | 88 | 1 | 3 | F2:4 family mean of 5 plants |
| 7AO-2065-0 | 3.6 | 3 | 88 | 1 | 3 | F2:4 family mean of 3 plants |
| 7AO-2082-0 | 3.6 | 3 | 88 | 2 | 3 | F2:4 family mean of 5 plants |
| 7AO-2068-0 | 3.6 | 3 | 88 | 1 | 3 | F2:4 family mean of 4 plants |
| 7AO-2079-0 | 3.6 | 3 | 88 | 1 | 3 | F2:4 family mean of 12 plants |

Example 8

Soybeans with High Oleic Acid and Low Linolenic Acid Content

Crosses were made between soybean lines containing the D2T gene for high oleic acid content and soybean lines containing either a fan allele or the D3A gene for low linolenic acid content to obtain F1 progeny. F1 progeny were then selfed in subsequent generations to obtain F2 seeds and F2:3 families. F2:3 families containing both minimum linolenic acid content and maximum oleic acid content were then selected and planted and allowed to self pollinate in order to obtain F3:4 progenies. A sample of F4 seed from each F3 plant (F3:4 seed) was then submitted for GC analysis so that individual F3:4 phenotypes could be determined. F3:4 plant phenotypes tracing back to a common F2 plant ancestor were then averaged to obtain mean phenotypes for F2-derived families (F2:4 family means). Single plants and family means that were both lowest in linolenic acid content and highest in oleic acid content are shown in Table 12, and are presented in order of increasing linolenic acid. Since selection for low linolenic acid content requires precision to a tenth of a percent, linolenic acid values in Table 12 are shown to that level of precision while values for the other fatty acids are rounded to the nearest whole percent.

TABLE 12

Individual Plants and F2:4 Family Mean Phenotypes
With a Combination of High Oleic and Low Linolenic Acid Content

| | Individual Fatty Acid Content (% of total seed fatty acid) | | | | | |
|---|---|---|---|---|---|---|
| Line ID | 16:0 | 18:0 | 18:1 | 18:2 | 18:3 | generation and type |
| 7OL-2703-6 | 5 | 3 | 87 | 2 | 1.7 | F3:4 single plant |
| 7OL-2708-1 | 7 | 4 | 85 | 1 | 1.7 | F3:4 single plant |
| 7OL-2703-7 | 6 | 3 | 87 | 1 | 1.8 | F3:4 single plant |
| 7OL-2706-6 | 6 | 4 | 86 | 1 | 1.8 | F3:4 single plant |
| 7OL-2703-5 | 5 | 3 | 88 | 1 | 1.9 | F3:4 single plant |
| 7OL-2703-2 | 6 | 3 | 87 | 1 | 1.9 | F3:4 single plant |
| 7OL-5180-7 | 6 | 3 | 87 | 2 | 1.9 | F3:4 single plant |
| 7OL-5181-7 | 6 | 3 | 86 | 2 | 1.9 | F3:4 single plant |
| 7OL-2706-7 | 6 | 4 | 86 | 1 | 1.9 | F3:4 single plant |
| 7OL-2707-5 | 6 | 4 | 86 | 1 | 1.9 | F3:4 single plant |
| 7OL-2705-10 | 7 | 4 | 85 | 1 | 1.9 | F3:4 single plant |
| 7OL-2711-4 | 7 | 4 | 85 | 2 | 1.9 | F3:4 single plant |
| 7OL-2712-5 | 7 | 4 | 84 | 2 | 1.9 | F3:4 single plant |
| 7OL-2708-0 | 7 | 5 | 84 | 1 | 1.8 | F2:4 family mean of 4 plants |
| 7OL-2703-0 | 6 | 3 | 87 | 1 | 1.9 | F2:4 family mean of 7 plants |
| 7OL-2707-0 | 6 | 4 | 86 | 1 | 2.1 | F2:4 family mean of 5 plants |
| 7OL-2705-0 | 6 | 4 | 85 | 1 | 2.1 | F2:4 family mean of 12 plants |
| 7OL-2710-0 | 7 | 4 | 85 | 2 | 2.2 | F2:4 family mean of 9 plants |
| 7OL-2711-0 | 7 | 4 | 84 | 2 | 2.2 | F2:4 family mean of 5 plants |
| 7OL-2712-0 | 7 | 5 | 82 | 3 | 2.3 | F2:4 family mean of 11 plants |
| 7OL-2713-0 | 6 | 4 | 85 | 2 | 2.4 | F2:4 family mean of 11 plants |
| 7OL-2709-0 | 7 | 4 | 83 | 2 | 2.5 | F2:4 family mean of 11 plants |

Example 9

Isolation of cDNA from *Brassica napus* Encoding acyl-ACP Thioesterase

A cDNA library was prepared from mRNA isolated from developing seeds of *Brassica napus* harvested from pods that were between 20 and 26 days post pollination. Total RNA was extracted and mRNA purified by oligo dT chromatography. The library was made by the technique described by Ray and Ray (1991, *Nucleic Acids Research* 19: 4559) using reagents purchased from Pharmacia, with some modifications. The resulting cDNA was cloned into the Lambda ZAP vector (Stratagene, La Jolla, Calif.) as per the manufacturer's instructions. The primary library contained approximately $1 \times 10^6$ individuals and was amplified once.

Cloning techniques used were from Sambrook et al. [(1989) Molecular Cloning: A Laboratory Manual, $2^{nd}$ Edition, Cold Spring Harbor Laboratory Press]. Approximately $3 \times 10^5$ plaques from the amplified library were developed by infection of *E. coli* plated on a total of six plates and duplicate nitrocellulose lifts were taken from each developed plate. The duplicate nitrocellulose lifts were probed with the $^{32}$P labeled (random primer labeling kit, Life Technologies, Gaithersburg, Md.) sequence from the *Brasica* genomic clone (SEQ ID NO:20 in WO 92/11373) and annealed at 63° in hybridizaion buffer (6×SSC [0.9 M NaCl, 0.09 M sodium citrate, pH 7], 5× Denhardts's solution [0.5 g Ficoll (type 400, Pharmacia), 0.5 g polyvinylpyrrolidone, 0.5 g bovine serum albumin (fraction V, Sigma), 1 mM EDTA, 1% SDS and 100 micrograms denatured salmon sperm DNA/ml (Sigma). The lifts were annealed for 18 hr, then washed at 63° in 0.2×SSC and placed on photographic film. Sixteen plaques were scored as hybridizing to the probe, and of these seven were purified and excised according to directions in the Lambda ZAP Cloning Instruction Kit Manual (Stratagene). The resulting phagemids were used to infect *E. coli* XL1 Blue cells, and resulted in double stranded plasmids containing the selected cDNA inserts. Two classes of clones were indicated by restriction analysis of the purified plasmids. One class was represented by a clone designated p5C. The insert in p5C was sequenced by dideoxy sequencing and was confirmed as encoding the *Brassica napus* oleoyl-ACP thioesterase. The sequence of this cDNA in shown in SEQ ID NO:1. The sequence of the encoded protein is shown in SEQ ID NO:2. The predicted translation product is 98.6% identical to the protein encoded by another cDNA reported by Jones et al. (1995, *Plant Cell* 7:359–371) and submitted to GenBank with accession number U17098. The sequences of this second thioesterase clone and the protein are presented in SEQ ID NO:3 and 4, respectively.

Example 10

Expression of the Oleoyl-ACP Thioesterase from *Brassica napus* in Soybean Seeds The entire cDNA insert in p5C was released from pBluescript as an Xmn I fragment and cloned into a soybean seed expression vector for use in biolistic transformation of elite soybean cultivar A2396.

A plasmid was constructed in which the acyl-ACP (oleoyl-ACP) thioesterase from *Brassica napus* cDNA sequence was placed under the control of the soybean beta-conglycinin promoter (Beachy R N. et al. (1985) *EMBO J.* 4:3047–3053). The construction of this vector was facilitated by the use of plasmid pCW109, described in WO 94/11516. Vector pCW109 contains an 830 base DNA segment which includes the promoter sequences for the alpha subunit of the soybean seed storage protein beta conglycinin, a region with multiple restriction sites, and 1080 bases of 3' regulatory sequence from the common bean seed storage protein, phaseolin. Vector pCW109 was modified to contain a Sma I site in the multiple cloning region as well. The cDNA insert of p5C was removed by digestion with Xmn I, isolated, and ligated into the modified pCW109 which had been digested with SmaI and an event in which the cDNA insert from p5C was oriented in the sense direction was chosen and designated pST14.

A plasmid designated pKS18HH was constructed to allow conferred resistance to hygromycin B to either plants or bacteria transformed with the plasmid. The plasmid was constructed using the following genetic elements: 1) plasmid vector pSP72 (Promega, Madison, Wis.), which was modified by removal of the β-lactamase coding region, 2) a plant selectable marker cassette consisting of the 35S promoter from cauliflower mosaic virus (CaMV) linked to the hygromycin B phosphotransferase (HPT) and the nopaline synthase 3' regulatory sequence from *Agrobacterium tumefaciens,* and 3) a bacterial selectable marker cassette consisting of the promoter from bacteriophage T7, a Shine-Dalgarno sequence upstream of the HPT coding sequence, and the T7 transcription terminator sequence.

The hygromycin B phosphotransferase gene was obtained from *E. coli* strain W677 which contained a Klebsiella-derive plasmid (pJR225, Gritz, L. and Davies, J. (1983) *GENE* 25:179–188). The T7 promoter:HPT:T7 terminator cassette for expression of the HPT enzyme in certain strains of E. coli, such as NovaBlue (Novagen, Madison, Wis.) was obtained from a derivative of a pET vector. The origin of the 35S:HPT:Nopaline synthase 3' end cassette for expression of HPT in plant is described in detail WO 94/11516.

One skilled in the art can incorporate these elements into a single plasmid using the usual protocols of molecular cloning.

To allow use of the vector in the transformation protocol described by Christou et al. (1990, *Trends Biotech* 8:145) the HPT encoding sequence in the 35S:HPT:Nopaline synthase cassette was removed by restriction endonuclease digestion and replaced by the correctly oriented coding region for the bacterial β-glucuronidase gene (Jefferson et al. (1987) *EMBO J.* 6:3901–3907). The resulting plasmid was designated pKS18.

The β-conglycinin:p5C:phaseolin-3' expression cassette in pST14 was removed by a partial HindIII digestion, isolated and ligated into pKS18 that had also been digested with HindIII to give the final transformation vector designated pRB19.

The transformation technique gives plants which set seeds that may be segregating for the introduced transgene. The bulked seed from the plants may also be chimeric for the transgene.

Three fertile plants were recovered from the transformation and the seeds were analyzed for their fatty acid phenotype by a partial seed analysis technique. A small chip of cotyledon oriented away from the embryonic axis was cut from the seed with a razor blade. The chip was digested in methanol containing 1% sodium methoxide and the resulting fatty acid methyl esters were extracted into hexane prior to separation and quantification by gas liquid chromatography. Seeds with altered fatty acid profiles were thus identified for subsequent germination and growth.

Of the three soybean plants transformed with the seed expression vector containing the *Brassica* acyl-ACP thioesterase, one had no alteration in seed fatty acid phenotype (32 seeds analyzed with a mean of 3.9% stearic acid and an observed range of 3.2% to 4.6%). The two remaining plants had an increased stearic acid content in their seeds. Twenty-nine seeds were analyzed from the second plant, and were determined to have a mean stearic acid content of 5.4% with an observed range from 3.8% to 7.5%, while forty seeds were analyzed from the third plant and were determined to have a mean stearic acid content of 4.85 and an observed range from 3.5 to 6.7%.

In seeds selected from the initial transformant on the basis of elevated levels of 16:0 and 18:0, progeny were selected in subsequent generations that had consistently elevated levels of the saturated fatty acids stearic acid and palmitic acid. Stearic acid level was increased by about two- to three-fold while the palmitic acid level increased by about 25 to 40% over typical, non-transformed elite lines. The stable line that was obtained from this transformation was designated T1S. It has been deposited with the American Type Culture Collection, Manassas, Va.

Example 11

Soybean with Very High Stearic Acid Content Resulting from Combined Alterations of Stearoyl-ACP Desaturase and Oleoyl-ACP Thioesterase Crosses were made between soybean lines containing a fasa allele and soybean lines containing the T1S gene (increasing oleoyl ACP thioesterase) to obtain F1 progeny. The intent is to accumulate stearoyl-ACP which is subsequently cleaved by the thioesterase resulting in the accumulation of stearic acid in the seed. F1 progeny were then selfed in subsequent generations to obtain F2 seeds and F2:3 families. F2:3 families containing elevated levels of both palmitic and stearic acid were then selected and planted and allowed to self pollinate in order to obtain F3:4 progenies. A sample of F4 seed from each F3 plant (F3:4 seed) was then submitted for GC analysis so that individual F3:4 phenotypes could be determined. Single plant fatty acid profiles are shown in Table 13, and are presented in order of increasing total seed saturated fatty acids.

TABLE 13

Fatty acid profiles of individual plants with high saturated fatty acid content due to increased oleoyl-ACP thioesterase and decreased stearoyl-ACP desaturase

| | Individual Fatty Acid Content (% of total seed fatty acid) | | | | | |
|---|---|---|---|---|---|---|
| Line ID | 16:0 | 18:0 | 18:1 | 18:2 | 18:3 | generation and type |
| 7S-2244-6 | 16 | 36 | 7 | 33 | 7 | F3:4 single plant |
| 7S-2244-7 | 15 | 35 | 8 | 34 | 7 | F3:4 single plant |
| 7S-2244-3 | 15 | 35 | 7 | 34 | 7 | F3:4 single plant |
| 7S-2236-4 | 13 | 35 | 15 | 30 | 6 | F3:4 single plant |
| 7S-2236-2 | 14 | 33 | 9 | 37 | 7 | F3:4 single plant |
| 7S-2236-6 | 13 | 34 | 9 | 36 | 6 | F3:4 single plant |
| 7S-2236-7 | 13 | 34 | 9 | 36 | 6 | F3:4 single plant |
| 7S-2244-1 | 14 | 32 | 9 | 37 | 7 | F3:4 single plant |
| 7S-2244-4 | 14 | 32 | 9 | 37 | 7 | F3:4 single plant |
| 7S-2244-5 | 14 | 32 | 9 | 37 | 7 | F3:4 single plant |
| 7S-2236-3 | 15 | 30 | 11 | 37 | 6 | F3:4 single plant |
| 7S-2240-3 | 12 | 33 | 13 | 35 | 6 | F3:4 single plant |
| 7S-2240-2 | 12 | 32 | 11 | 37 | 6 | F3:4 single plant |
| 7S-2240-4 | 12 | 31 | 13 | 37 | 6 | F3:4 single plant |
| 7S-2240-5 | 12 | 31 | 11 | 38 | 6 | F3:4 single plant |
| 7S-2240-1 | 12 | 29 | 13 | 39 | 6 | F3:4 single plant |
| 7S-2236-1 | 13 | 25 | 11 | 42 | 7 | F3:4 single plant |

Example 12

Solid Fat Content of a Very High Stearic Soybean Oils

Very high stearic acid soybeans were obtained from plants described in Example 11. Oils were prepared from the seeds, as described in Example 1, and analyzed for fatty acid composition and solid fat content at a variety of temperatures.

Figure 4:
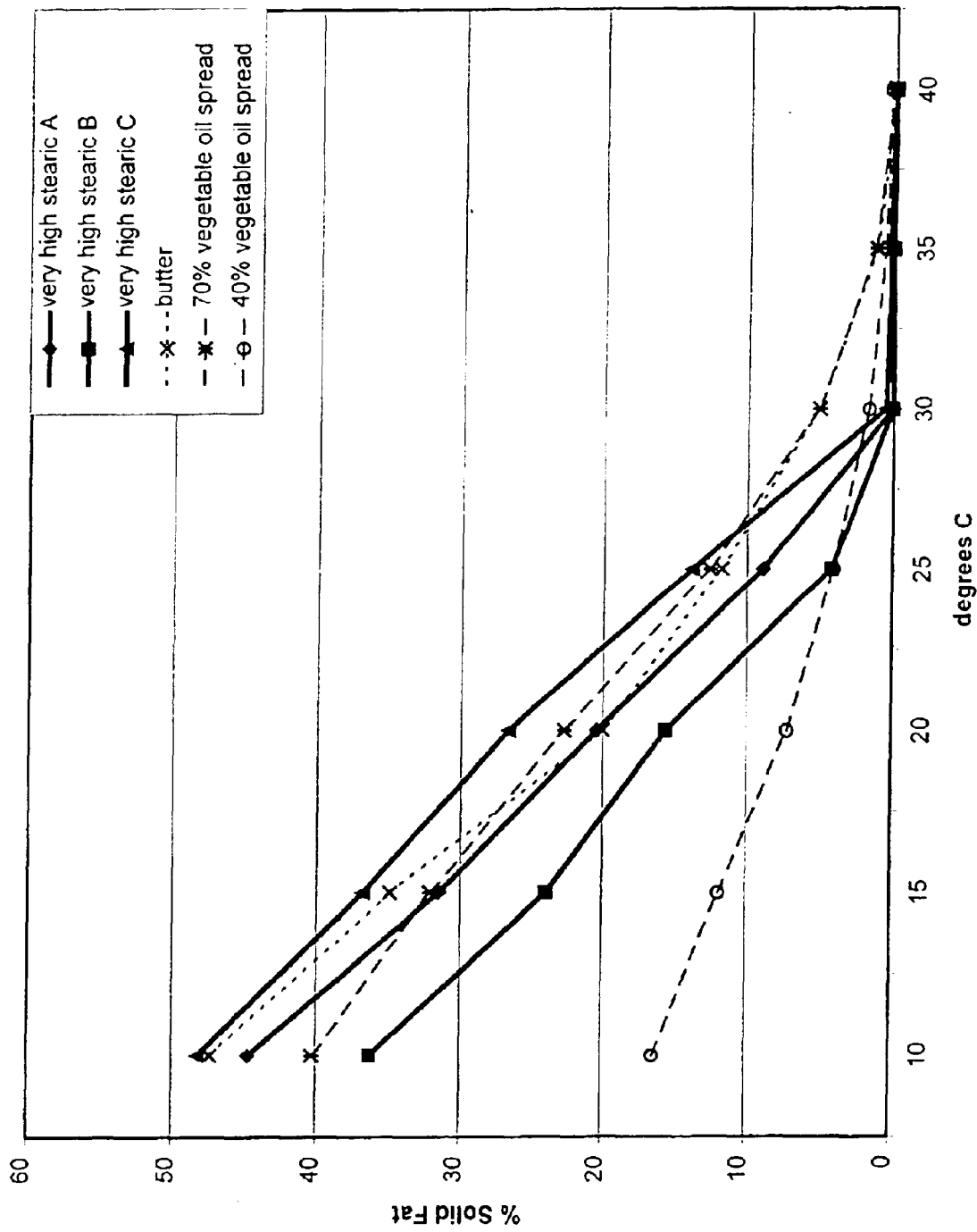
FIG. 4 shows that very high stearic acid oils have SFC profiles consistent with butter and hardstock oils.

Tables 14 and 15 show the compositional and functional characteristics of very high stearic soybean oils ranging from 33% to 38% stearic acid. All of the oils met the solidity requirements for a margarine (for comparison see curves in FIG. 1). The SFC profiles for these high stearic oils are consistent with those obtained from stick margarines or butter (see FIG. 4). It is believed that the oils derived from Example 11, as well as oils with similar compositions, will be capable of producing fat products with SFC profiles of less than 20 at 25° C., preferably less hand 15 at 25° C., more preferably less than 10 at 25° C., and most preferably less than 5 at 25° C., and greater than 20 at 10° C., preferably between 20 and 50 at 10° C., and most preferably between 35 and 50 at 10° C. Therefore, these oils could be useful for producing stick margarines that are substantially free of trans fatty acids, or as a hardstock additive in blends to produce margarines or oil-based spreads.

TABLE 14

Fatty acid composition

|  | 16:0 | 18:0 | 18:1 | 18:2 | 18:3 | 20:0 |
|---|---|---|---|---|---|---|
| Very high stearic A | 14.4 | 35.4 | 8.8 | 33.2 | 5.0 | 1.7 |
| Very high stearic B | 14.0 | 33.6 | 9.1 | 34.8 | 5.4 | 1.6 |
| Very high stearic C | 13.5 | 38.2 | 8.3 | 30.9 | 5.5 | 1.9 |

TABLE 15

SFC as a function of temperature

| SFC % | Temperature: | | | | | | |
|---|---|---|---|---|---|---|---|
|  | 10° | 15° | 20° | 25° | 30° | 35° | 40° |
| Very high stearic A | 44.7 | 31.5 | 20.4 | 8.9 | 0 | 0.3 | 0 |
| Very high stearic B | 36.3 | 23.9 | 15.6 | 4.2 | 0 | 0.1 | 0 |
| Very high stearic C | 48.2 | 36.8 | 26.6 | 13.8 | 0.5 | 0.2 | 0 |

Example 13

Alternative Method to Produce High Oleic and Low Saturated Fatty Acid Soybeans The promoter:palmitoyl-ACP thioesterase coding region plant transformation vector described in WO9606936 was used to transform soybean somatic embryo producing cultures and transformed, fertile soybean plants were obtained again using the methods detailed in WO9606936. The fatty acid profile of seed chips removed from mature cotyledons of the seed born on the transgenic plants was determined. A small fraction of the plants had seeds that appeared to be segregating for a very low saturated fatty acid phenotype. Three such plants were identified; the low saturate class for all three transgenic events averaged a combined 16:0+18:0 content of 5.6% of the total fatty acids while the normal saturated fatty acid classes averaged 14.9%.

The total fatty acid profile averaged from 228 seed chips from the low saturated fatty acid class of seeds from three plants combined from the best event is given in Table 16.

TABLE 16

Fatty Acid Profiles for Three Palmitoyl-ACP Thioesterase Co-Suppressed Soybean Plants Useful as One of the Parents in the Production of High Oleic and Low Saturated Fatty Acid Soybeans
Each Class, % of Total Fatty Acids

| 16:0 | 18:0 | 18:1 | 18:2 | 18:3 |
|---|---|---|---|---|
| 2.6 | 2.4 | 17.3 | 65.3 | 12.4 |

To produce a high oleic, low saturated fatty acid seed phenotype using the above described plants as the low saturate parent, seed remaining from the seed chip analysis is planted and taken to flowering. Reciprocal crosses are made between the palmitoyl-ACP thioesterase co-suppression plants and the fatty acid delta-12 desaturase co-suppression plants. Since, at planting, the low saturate seed could have been from either, a seed homozygous for the transgene, or heterozygous for the transgene, remaining flowers on the parental plants are allowed to self-pollinate. The segregation pattern in the self-pollination produced seed is determined to identify plants that are homozygous for the low saturated fatty acid transgene as indicated by the absence of nornal saturated fatty acid seeds. Seed from crosses, that are made to plants homozygous for the low saturated fatty acid transgene, are planted. The flowers are allowed to self pollinate and the seed, segregating for both the high oleic and low saturated fatty acid phenotypes is analyzed by the seed chip method. Remaining seed from seed chips showing the desired phenotype is planted, the plants are self-pollinated and bulked seed from individual plants is analyzed to confirm the desired phenotype.

What is claimed is:

1. A soybean plant that produces mature seeds in which the total seed fatty acid profile comprises a C16:0 content of greater than 10%, a combined C16:0 and C18:0 content of greater than 30%, a C18:1 content of greater than 55% and a combined C18:2 and C18:3 content of less than 7%.

2. A soybean plant of claim 1 wherein said plant is produced by the following steps which comprise:
   (a) crossing a first parent soybean plant wherein the C18:1 content comprises at least 80% of the total seed fatty acid and the first parent further comprises at least one transgene copy of a soybean nucleic acid fragment encoding a delta-12 desaturase enzyme with a second parent comprising a fasa allele for elevated seed stearic acid content and a fap2 allele for elevated seed palmitic acid;
   (b) obtaining hybrid seeds from the cross of step (a), germinating said seeds, growing and producing a segregating population of soybean plants through one or more cycles of self-pollination; and
   (c) selecting the plants from the segregating population of step (b) which produce seeds having said fatty acid profile.

3. Seeds obtained from the plant of claim 1.

* * * * *

SEQUENCE LISTING

<160> NUMBER OF SEQ ID NOS: 4

<210> SEQ ID NO 1
<211> LENGTH: 1412
<212> TYPE: DNA
<213> ORGANISM: Brassica napus
<220> FEATURE:
<221> NAME/KEY: CDS
<222> LOCATION: (36)..(1124)
<220> FEATURE:
<221> NAME/KEY: mat_peptide
<222> LOCATION: (210)..(1124)

<400> SEQUENCE: 1

```
cggcacgaga cattttcttc ttcgatcccg aaaag atg ttg aag ctc tcg tgt      53
                                    Met Leu Lys Leu Ser Cys
                                                        -55 aat gcg act gat aag tta cag acc ctc ttc tcg cat tct cat caa ccg   101
Asn Ala Thr Asp Lys Leu Gln Thr Leu Phe Ser His Ser His Gln Pro
    -50                 -45                 -40 gat ccg gca cac cgg aga acc gtc tcc tcc gtg tcg tgc tct cat ctg   149
Asp Pro Ala His Arg Arg Thr Val Ser Ser Val Ser Cys Ser His Leu
        -35                 -30                 -25
```

-continued

| | | |
|---|---|---|
| agg aaa ccg gtt ctc gat cct ttg cga gcg atc gta tct gct gat caa<br>Arg Lys Pro Val Leu Asp Pro Leu Arg Ala Ile Val Ser Ala Asp Gln<br>-20                          -15                                 -10                                 -5 | 197 | |
| gga agt gtg att cga gca gaa caa ggt ttg ggc tca ctc gcg gat cag<br>Gly Ser Val Ile Arg Ala Glu Gln Gly Leu Gly Ser Leu Ala Asp Gln<br>           -1  1                                 5                                 10 | 245 | |
| ctc cga ttg ggt agc ttg acg gag gat ggt ttg tcg tat aag gag aag<br>Leu Arg Leu Gly Ser Leu Thr Glu Asp Gly Leu Ser Tyr Lys Glu Lys<br>        15                       20                       25 | 293 | |
| ttc atc gtc aga tcc tac gag gtt ggg agt aac aag acc gcc act gtc<br>Phe Ile Val Arg Ser Tyr Glu Val Gly Ser Asn Lys Thr Ala Thr Val<br>        30                       35                       40 | 341 | |
| gaa acc gtc gct aat ctt ttg cag gag gtg gga tgt aat cat gcg cag<br>Glu Thr Val Ala Asn Leu Leu Gln Glu Val Gly Cys Asn His Ala Gln<br>45                          50                       55                       60 | 389 | |
| agc gtt gga ttc tcg act gat ggg ttt gcg aca aca ccg aca atg agg<br>Ser Val Gly Phe Ser Thr Asp Gly Phe Ala Thr Thr Pro Thr Met Arg<br>                 65                       70                       75 | 437 | |
| aaa ctg cat ctc att tgg gtc act gcg aga atg cat ata gag atc tac<br>Lys Leu His Leu Ile Trp Val Thr Ala Arg Met His Ile Glu Ile Tyr<br>               80                       85                       90 | 485 | |
| aag tac cct gct tgg ggt gat gtg gtt gag ata gag aca tgg tgt cag<br>Lys Tyr Pro Ala Trp Gly Asp Val Val Glu Ile Glu Thr Trp Cys Gln<br>               95                     100                    105 | 533 | |
| agt gaa gga agg atc ggg act agg cgt gat tgg att ctt aag gat gtt<br>Ser Glu Gly Arg Ile Gly Thr Arg Arg Asp Trp Ile Leu Lys Asp Val<br>        110                     115                      120 | 581 | |
| gct acg ggt gaa gtc act ggc cgt gct aca agc aag tgg gtg atg atg<br>Ala Thr Gly Glu Val Thr Gly Arg Ala Thr Ser Lys Trp Val Met Met<br>125                        130                      135                   140 | 629 | |
| aac caa gac aca aga cgg ctt cag aaa gtt tct gat gat gtt cgg gac<br>Asn Gln Asp Thr Arg Arg Leu Gln Lys Val Ser Asp Asp Val Arg Asp<br>                     145                      150                    155 | 677 | |
| gag tac ttg gtc ttc tgt cct aaa gaa ctc aga tta gca ttt cct gag<br>Glu Tyr Leu Val Phe Cys Pro Lys Glu Leu Arg Leu Ala Phe Pro Glu<br>        160                     165                      170 | 725 | |
| gag aat aac aga agc ttg aag aaa atc cca aaa ctc gaa tat cca gct<br>Glu Asn Asn Arg Ser Leu Lys Lys Ile Pro Lys Leu Glu Tyr Pro Ala<br>        175                     180                      185 | 773 | |
| cag tat tca atg att ggt ctt aag cct aga cga gct gat ctc gac atg<br>Gln Tyr Ser Met Ile Gly Leu Lys Pro Arg Arg Ala Asp Leu Asp Met<br>        190                     195                      200 | 821 | |
| aac cag cat gtc aat aat gtc acc tat att gga tgg gtt ctt gag agc<br>Asn Gln His Val Asn Asn Val Thr Tyr Ile Gly Trp Val Leu Glu Ser<br>205                        210                      215                   220 | 869 | |
| ata cct caa gag att gta gac acg cac gaa ctt cag gtc ata act ctg<br>Ile Pro Gln Glu Ile Val Asp Thr His Glu Leu Gln Val Ile Thr Leu<br>                     225                      230                    235 | 917 | |
| gat tac aga aga gaa tgt caa caa gac gat gtg gtg gat tca ctc acc<br>Asp Tyr Arg Arg Glu Cys Gln Gln Asp Asp Val Val Asp Ser Leu Thr<br>        240                     245                      250 | 965 | |
| act acc acc tca gag att ggt ggg acc aat ggc tct gca aca tca gcc<br>Thr Thr Thr Ser Glu Ile Gly Gly Thr Asn Gly Ser Ala Thr Ser Ala<br>        255                     260                      265 | 1013 | |
| gca caa ggc cac aac gat agc cag ttc tta cat ctc cta agg ttg tct<br>Ala Gln Gly His Asn Asp Ser Gln Phe Leu His Leu Leu Arg Leu Ser<br>270                        275                      280 | 1061 | |
| gga gac ggt cag gag atc aac cgc ggg aca acc ctg tgg aga aag aag<br>Gly Asp Gly Gln Glu Ile Asn Arg Gly Thr Thr Leu Trp Arg Lys Lys<br>285                        290                      295                   300 | 1109 | |

```
ccc tcc aat ctc taa gccatttcgt tcttaagttt cctctatctg tgtcgctgat    1164
Pro Ser Asn Leu
            305 gcttcacgag tctagtcagg tctcattttt ttcaatataa atttgggtta gactagagaa    1224 ctggaattat tggaatttat gagttttcgt tcttgtttct gtacaaatct tgaggattga    1284 agccaaaccc atttcatctt agtctcttcc ggtcttgtct tgtgtctctg cgtgtatctt    1344 atcgaaaact taaacaaaaa aagattgctt ttcatatgtt cttataataa aaggagttac    1404 tttgacat                                                             1412

<210> SEQ ID NO 2
<211> LENGTH: 362
<212> TYPE: PRT
<213> ORGANISM: Brassica napus

<400> SEQUENCE: 2
```

Met Leu Lys Leu Ser Cys Asn Ala Thr Asp Lys Leu Gln Thr Leu Phe
1               5                   10                  15

Ser His Ser His Gln Pro Asp Pro Ala His Arg Arg Thr Val Ser Ser
            20                  25                  30

Val Ser Cys Ser His Leu Arg Lys Pro Val Leu Asp Pro Leu Arg Ala
        35                  40                  45

Ile Val Ser Ala Asp Gln Gly Ser Val Ile Arg Ala Glu Gln Gly Leu
    50                  55                  60

Gly Ser Leu Ala Asp Gln Leu Arg Leu Gly Ser Leu Thr Glu Asp Gly
65                  70                  75                  80

Leu Ser Tyr Lys Glu Lys Phe Ile Val Arg Ser Tyr Glu Val Gly Ser
                85                  90                  95

Asn Lys Thr Ala Thr Val Glu Thr Val Ala Asn Leu Leu Gln Glu Val
            100                 105                 110

Gly Cys Asn His Ala Gln Ser Val Gly Phe Ser Thr Asp Gly Phe Ala
        115                 120                 125

Thr Thr Pro Thr Met Arg Lys Leu His Leu Ile Trp Val Thr Ala Arg
    130                 135                 140

Met His Ile Glu Ile Tyr Lys Tyr Pro Ala Trp Gly Asp Val Val Glu
145                 150                 155                 160

Ile Glu Thr Trp Cys Gln Ser Glu Gly Arg Ile Gly Thr Arg Arg Asp
                165                 170                 175

Trp Ile Leu Lys Asp Val Ala Thr Gly Glu Val Thr Gly Arg Ala Thr
            180                 185                 190

Ser Lys Trp Val Met Met Asn Gln Asp Thr Arg Arg Leu Gln Lys Val
        195                 200                 205

Ser Asp Asp Val Arg Asp Glu Tyr Leu Val Phe Cys Pro Lys Glu Leu
    210                 215                 220

Arg Leu Ala Phe Pro Glu Glu Asn Asn Arg Ser Leu Lys Lys Ile Pro
225                 230                 235                 240

Lys Leu Glu Tyr Pro Ala Gln Tyr Ser Met Ile Gly Leu Lys Pro Arg
                245                 250                 255

Arg Ala Asp Leu Asp Met Asn Gln His Val Asn Asn Val Thr Tyr Ile
            260                 265                 270

Gly Trp Val Leu Glu Ser Ile Pro Gln Glu Ile Val Asp Thr His Glu
        275                 280                 285

Leu Gln Val Ile Thr Leu Asp Tyr Arg Arg Glu Cys Gln Gln Asp Asp
    290                 295                 300

```
Val Val Asp Ser Leu Thr Thr Thr Ser Glu Ile Gly Gly Thr Asn
305                 310                 315                 320

Gly Ser Ala Thr Ser Ala Ala Gln Gly His Asn Asp Ser Gln Phe Leu
            325                 330                 335

His Leu Leu Arg Leu Ser Gly Asp Gly Gln Glu Ile Asn Arg Gly Thr
                340                 345                 350

Thr Leu Trp Arg Lys Lys Pro Ser Asn Leu
            355                 360

<210> SEQ ID NO 3
<211> LENGTH: 1307
<212> TYPE: DNA
<213> ORGANISM: Brassica napus
<220> FEATURE:
<221> NAME/KEY: CDS
<222> LOCATION: (38)..(1126)
<300> PUBLICATION INFORMATION:
<303> JOURNAL: Plant Cell
<304> VOLUME: 7
<306> PAGES: 359-371
<308> DATABASE ACCESSION NUMBER: U17098
<309> DATABASE ENTRY DATE: 1995-06-01

<400> SEQUENCE: 3
gctcgcctcc cacattttct tcttcgatcc cgaaaag atg ttg aag ctc tcg tgt       55
                                         Met Leu Lys Leu Ser Cys
                                         1               5 aat gcg act gat aag tta cag acc ctc ttc tcg cat tct cat caa ccg      103
Asn Ala Thr Asp Lys Leu Gln Thr Leu Phe Ser His Ser His Gln Pro
        10                  15                  20 gat ccg gca cac cgg aga acc gtc tcc tcc gtg tcg tgc tct cat ctg      151
Asp Pro Ala His Arg Arg Thr Val Ser Ser Val Ser Cys Ser His Leu
    25                  30                  35 agg aaa ccg gtt ctc gat cct ttg cga gcg atc gta tct gct gat caa      199
Arg Lys Pro Val Leu Asp Pro Leu Arg Ala Ile Val Ser Ala Asp Gln
40                  45                  50 gga agt gtg att cga gca gaa caa ggt ttg ggc tca ctc gcg gat cag      247
Gly Ser Val Ile Arg Ala Glu Gln Gly Leu Gly Ser Leu Ala Asp Gln
55                  60                  65                  70 ctc cga ttg ggt agc ttg acg gag gat ggt ttg tcg tat aag gag aag      295
Leu Arg Leu Gly Ser Leu Thr Glu Asp Gly Leu Ser Tyr Lys Glu Lys
                75                  80                  85 ttc atc gtc aga tcc tac gaa gtg ggg agt aac aag acc gcc act gtc      343
Phe Ile Val Arg Ser Tyr Glu Val Gly Ser Asn Lys Thr Ala Thr Val
            90                  95                  100 gaa acc gtc gct aat ctt ttg cag gag gtg gga tgt aat cat gcg cag      391
Glu Thr Val Ala Asn Leu Leu Gln Glu Val Gly Cys Asn His Ala Gln
        105                 110                 115 agc gtt gga ttc tcg act gat ggg ttt gcg aca aca ccg acc atg agg      439
Ser Val Gly Phe Ser Thr Asp Gly Phe Ala Thr Thr Pro Thr Met Arg
    120                 125                 130 aaa ctg cat ctc att tgg gtc act gcg aga atg cat ata gag atc tac      487
Lys Leu His Leu Ile Trp Val Thr Ala Arg Met His Ile Glu Ile Tyr
135                 140                 145                 150 aag tac cct gct tgg ggt gat gtg gtt gag ata gag aca tgg tgt cag      535
Lys Tyr Pro Ala Trp Gly Asp Val Val Glu Ile Glu Thr Trp Cys Gln
                155                 160                 165 agt gaa gga agg atc ggg act agg cgt gat tgg att ctt aag gat gtt      583
Ser Glu Gly Arg Ile Gly Thr Arg Arg Asp Trp Ile Leu Lys Asp Val
            170                 175                 180 gct acg ggt gaa gtc act ggc cgt gct aca agc aag tgg gtg atg atg      631
Ala Thr Gly Glu Val Thr Gly Arg Ala Thr Ser Lys Trp Val Met Met
```

-continued

| | | | | | | | | | | | | | | | |
|---|---|---|---|---|---|---|---|---|---|---|---|---|---|---|---|
| Ala | Thr | Gly | Glu | Val | Thr | Gly | Arg | Ala | Thr | Ser | Lys | Trp | Val | Met | Met |
| | | 185 | | | | 190 | | | | 195 | | | | | |

```
aac caa gac aca aga cgg ctt cag aaa gtt tct gat gat gtt cgg gac     679
Asn Gln Asp Thr Arg Arg Leu Gln Lys Val Ser Asp Asp Val Arg Asp
    200             205             210 gag tac ttg gtc ttc tgt cct aaa gaa ctc aga tta gca ttt cct gag     727
Glu Tyr Leu Val Phe Cys Pro Lys Glu Leu Arg Leu Ala Phe Pro Glu
215             220             225             230 gag aat aac aga agc ttg aag aaa att ccg aaa ctc gaa gat cca gct     775
Glu Asn Asn Arg Ser Leu Lys Lys Ile Pro Lys Leu Glu Asp Pro Ala
            235             240             245 cag tat tcg atg att ggg ctt aag cct aga cga gct gat ctc gac atg     823
Gln Tyr Ser Met Ile Gly Leu Lys Pro Arg Arg Ala Asp Leu Asp Met
        250             255             260 aac cag cat gtc aat aat gtc acc tat att gga tgg gtt ctt gag agc     871
Asn Gln His Val Asn Asn Val Thr Tyr Ile Gly Trp Val Leu Glu Ser
    265             270             275 ata cct caa gag att gta gac acg cac gaa ctt cag gtc ata act ctg     919
Ile Pro Gln Glu Ile Val Asp Thr His Glu Leu Gln Val Ile Thr Leu
280             285             290 gat tac aga aga gaa tgt caa caa gac gat gtg gtg gat tca ctc acc     967
Asp Tyr Arg Arg Glu Cys Gln Gln Asp Asp Val Val Asp Ser Leu Thr
295             300             305             310 act acc acc tca gag att ggt ggg acc aat ggc tct gca tca tca ggc    1015
Thr Thr Thr Ser Glu Ile Gly Gly Thr Asn Gly Ser Ala Ser Ser Gly
            315             320             325 aca cag ggg caa aac gat agc cag ttc tta cat ctc tta agg ctg tct    1063
Thr Gln Gly Gln Asn Asp Ser Gln Phe Leu His Leu Leu Arg Leu Ser
        330             335             340 gga gac ggt cag gag atc aac cgc ggg aca acc ctg tgg aga aag aag    1111
Gly Asp Gly Gln Glu Ile Asn Arg Gly Thr Thr Leu Trp Arg Lys Lys
    345             350             355 ccc tcc aat ctc taa gccatttcgt tcttaagttt cctctatctg tgtcgctcga    1166
Pro Ser Asn Leu
        360 tgcttcacga gtctagtcag gtctcatttt tttcaatcta aatttgggtt agactagaga  1226 actggaatta ttggaattta tgagttttcg ttcttgtttc tgtacaaatc ttgaggattg  1286 aagccaaacc catttcatct t                                            1307

<210> SEQ ID NO 4
<211> LENGTH: 362
<212> TYPE: PRT
<213> ORGANISM: Brassica napus

<400> SEQUENCE: 4

Met Leu Lys Leu Ser Cys Asn Ala Thr Asp Lys Leu Gln Thr Leu Phe
1               5                   10                  15

Ser His Ser His Gln Pro Asp Pro Ala His Arg Arg Thr Val Ser Ser
            20                  25                  30

Val Ser Cys Ser His Leu Arg Lys Pro Val Leu Asp Pro Leu Arg Ala
        35                  40                  45

Ile Val Ser Ala Asp Gln Gly Ser Val Ile Arg Ala Glu Gln Gly Leu
    50                  55                  60

Gly Ser Leu Ala Asp Gln Leu Arg Leu Gly Ser Leu Thr Glu Asp Gly
65                  70                  75                  80

Leu Ser Tyr Lys Glu Lys Phe Ile Val Arg Ser Tyr Glu Val Gly Ser
                85                  90                  95
```

-continued

```
Asn Lys Thr Ala Thr Val Glu Thr Val Ala Asn Leu Leu Gln Glu Val
            100                 105                 110

Gly Cys Asn His Ala Gln Ser Val Gly Phe Ser Thr Asp Gly Phe Ala
        115                 120                 125

Thr Thr Pro Thr Met Arg Lys Leu His Leu Ile Trp Val Thr Ala Arg
        130                 135                 140

Met His Ile Glu Ile Tyr Lys Tyr Pro Ala Trp Gly Asp Val Val Glu
145                 150                 155                 160

Ile Glu Thr Trp Cys Gln Ser Glu Gly Arg Ile Gly Thr Arg Arg Asp
                165                 170                 175

Trp Ile Leu Lys Asp Val Ala Thr Gly Glu Val Thr Gly Arg Ala Thr
            180                 185                 190

Ser Lys Trp Val Met Met Asn Gln Asp Thr Arg Arg Leu Gln Lys Val
            195                 200                 205

Ser Asp Asp Val Arg Asp Glu Tyr Leu Val Phe Cys Pro Lys Glu Leu
        210                 215                 220

Arg Leu Ala Phe Pro Glu Glu Asn Asn Arg Ser Leu Lys Lys Ile Pro
225                 230                 235                 240

Lys Leu Glu Asp Pro Ala Gln Tyr Ser Met Ile Gly Leu Lys Pro Arg
                245                 250                 255

Arg Ala Asp Leu Asp Met Asn Gln His Val Asn Asn Val Thr Tyr Ile
                260                 265                 270

Gly Trp Val Leu Glu Ser Ile Pro Gln Glu Ile Val Asp Thr His Glu
            275                 280                 285

Leu Gln Val Ile Thr Leu Asp Tyr Arg Arg Glu Cys Gln Gln Asp Asp
        290                 295                 300

Val Val Asp Ser Leu Thr Thr Thr Thr Ser Glu Ile Gly Gly Thr Asn
305                 310                 315                 320

Gly Ser Ala Ser Ser Gly Thr Gln Gly Gln Asn Asp Ser Gln Phe Leu
                325                 330                 335

His Leu Leu Arg Leu Ser Gly Asp Gly Gln Glu Ile Asn Arg Gly Thr
            340                 345                 350

Thr Leu Trp Arg Lys Lys Pro Ser Asn Leu
            355                 360
```